US010059922B2

(12) United States Patent
Sugarman

(10) Patent No.: US 10,059,922 B2
(45) Date of Patent: Aug. 28, 2018

(54) METHODS AND SYSTEMS FOR SEPARATING COMPONENTS OF A BIOLOGICAL SAMPLE WITH GRAVITY SEDIMENTATION

(71) Applicant: Becton, Dickinson and Company, Franklin Lakes, NJ (US)

(72) Inventor: Jeffrey Sugarman, Los Altos, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 106 days.

(21) Appl. No.: 15/314,640

(22) PCT Filed: Jul. 23, 2015

(86) PCT No.: PCT/US2015/041842
§ 371 (c)(1),
(2) Date: Nov. 29, 2016

(87) PCT Pub. No.: WO2016/018726
PCT Pub. Date: Feb. 4, 2016

(65) Prior Publication Data

US 2017/0121675 A1 May 4, 2017

Related U.S. Application Data

(60) Provisional application No. 62/031,753, filed on Jul. 31, 2014.

(51) Int. Cl.
*C12N 5/00* (2006.01)
*C12N 13/00* (2006.01)

(52) U.S. Cl.
CPC .......... *C12N 5/0087* (2013.01); *C12N 13/00* (2013.01)

(58) Field of Classification Search
CPC .......... C12N 1/00; C12N 1/20; C12N 5/0087; C12N 13/00; G01N 2035/00326; G01N 2035/00495; G01N 35/0092; G01N 35/00; G01N 35/1065; G01N 2015/1006; G01N 35/026; G01N 35/10; G01N 35/00871; G01N 35/1072; G01N 21/25; G01N 33/5005; G01N 15/1475; G01N 2035/00138; G01N 2035/00356; G01N 2035/00366; G01N 2035/00425; G01N 2035/0449; G01N 2035/0486; G01N 2035/0491; G01N 2201/024; G01N 2201/04; G01N 33/54366; G01N 35/00029; G01N 35/00069; G01N 35/04; G01N 35/1011; G01N 2015/0073; G01N 2015/008; G01N 2015/1486; G01N 2035/00148; G01N 2035/00237; G01N 2035/00306; G01N 2035/00435; G01N 2035/00633; G01N 2035/0474; G01N 2035/0493; G01N 2035/0494; G01N 21/27; G01N 2201/12; G01N 33/54306; G01N 33/54313; G01N 33/56983; G01N 33/62; G01N 33/6827; G01N 33/80; G01N 33/92; G01N 35/00623; G01N 35/1009; G01N 21/6428; G01N 33/50; G01N 2035/0094; G01N 2035/103; G01N 21/76; G01N 1/40; G01N 1/4077; G01N 2001/4083; G01N 2021/6441; G01N 2035/00881; G01N 21/07; G01N 21/75; G01N 21/78; G01N 30/88; G01N 15/14; G01N 2021/513; G01N 2021/6417; G01N 2021/825; G01N 2030/8827; G01N 2035/00811; G01N 2035/1048; G01N 21/21; G01N 21/35; G01N 21/4133; G01N 21/51; G01N 21/645; G01N 21/65; G01N 30/02; G01N 33/48;

(Continued)

(56) References Cited

U.S. PATENT DOCUMENTS

| | | | |
|---|---|---|---|
| 5,840,253 | A | 11/1998 | Chase et al. |
| 8,317,990 | B2 | 11/2012 | Pamula et al. |

(Continued)

FOREIGN PATENT DOCUMENTS

| | | |
|---|---|---|
| WO | WO2007120241 | 10/2007 |
| WO | WO20130746070 | 5/2013 |

(Continued)

OTHER PUBLICATIONS

Huh, et al. "Gravity-driven microfluidic particle sorting device with hydrodynamic separation amplification", Anal Chem. Feb. 15, 2007;79(4)1369-76.

(Continued)

*Primary Examiner* — Deborah K Ware
(74) *Attorney, Agent, or Firm* — Bret E. Field; Bozicevic, Field & Francis LLP

(57) ABSTRACT

Aspects of the present disclosure include methods for separating components having different densities from a biological sample droplet. Methods according to certain embodiments include contacting a surface of a support with a biological sample droplet that includes components of different densities; subjecting the biological sample droplet to a gravitational force to produce two or more regions in the biological sample droplet on the support surface, where each region in the biological sample droplet includes a component from the biological sample droplet having a different density; separating the biological sample droplet into two or more product droplets, wherein each product droplet includes a different region of the biological sample droplet; and collecting the one or more product droplets. Systems for practicing the subject methods are also described. Computer systems and kits are also provided.

20 Claims, 7 Drawing Sheets

(58) Field of Classification Search
CPC ............. G01N 33/5302; G01N 33/559; G01N 33/566; G01N 33/86; G01N 35/00732; G01N 35/0098; G01N 35/02; G01N 2035/1034; G01N 21/84; G01N 2035/00277; G01N 21/66; G01N 35/1095; B01L 7/52; B01L 9/06; B01L 2300/1855; B01L 3/5082; B01L 2300/1827; B01L 3/021; B01L 9/52; B01L 9/543; B01L 2200/0689; B01L 2400/0677; B01L 3/5021; B01L 3/0217; B01L 2200/028; B01L 2200/0631; B01L 2200/0647; B01L 2200/0684; B01L 2200/082; B01L 2200/141; B01L 2200/16; B01L 2300/044; B01L 2300/0829; B01L 2400/0409; B01L 2400/043; B01L 3/0279; B01L 3/50825; B01L 3/523; B01L 3/0275; B01L 3/502; B01L 1/00; B01L 2200/023; B01L 2200/025; B01L 2200/0673; B01L 2200/10; B01L 2300/041; B01L 2300/0851; B01L 2300/0893; B01L 3/502715; B01L 3/50851; B01L 3/50855; B01L 9/527; B01L 2200/04; B01L 2300/0654; B01L 9/523; C12Q 1/70; C12Q 1/42; C12Q 1/52; C12Q 1/6883; C12Q 1/68; C12Q 1/6806; C12Q 1/00; C12Q 1/02; C12Q 1/28; C12Q 1/6813; H05K 999/99; Y10T 436/111666; Y10T 436/113332; Y10T 436/25; Y10T 436/2575; Y10T 436/11; B04B 13/00; B04B 5/0414; B04B 5/0421; B04B 7/08; B04B 9/04; A61B 10/0045; A61B 2010/0003; A61B 5/0002; A61B 5/0022; A61B 5/688; A61B 5/7232; A61B 5/7275; A61B 5/74; A61B 8/483; G06F 19/3418; G06F 19/366; G16H 10/40; Y02A 90/26

See application file for complete search history.

(56) References Cited

U.S. PATENT DOCUMENTS

| | | | |
|---|---|---|---|
| 8,470,606 | B2 | 6/2013 | Srinivasan et al. |
| 8,613,889 | B2 | 12/2013 | Pollack et al. |
| 2007/0184463 | A1 | 8/2007 | Molho et al. |
| 2009/0283407 | A1 | 11/2009 | Shah et al. |
| 2010/0282608 | A1 | 11/2010 | Srinivasan et al. |
| 2011/0091989 | A1 | 4/2011 | Sista et al. |
| 2011/0114490 | A1 | 5/2011 | Pamula et al. |
| 2011/0186433 | A1 | 8/2011 | Pollack et al. |
| 2013/0178968 | A1 | 7/2013 | Sturmer et al. |
| 2014/0124037 | A1 | 5/2014 | Foley |

FOREIGN PATENT DOCUMENTS

| | | |
|---|---|---|
| WO | WO2013090889 | 6/2013 |
| WO | WO2014078100 | 5/2014 |

OTHER PUBLICATIONS

Park, et al. “Single-sided continuous optoelectrowetting (SCOEW) for droplet manipulation with light patterns”, Lab Chip. Jul. 7, 2010;10(13):1655-61.

Mugele, et al. “Electrowetting: from basics to applications”, J. Phys.: Condens. Matter 17 (2005) R705-R774.

110a
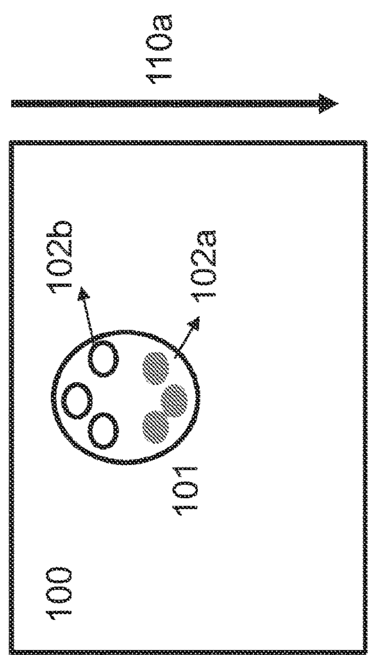
STEP 2
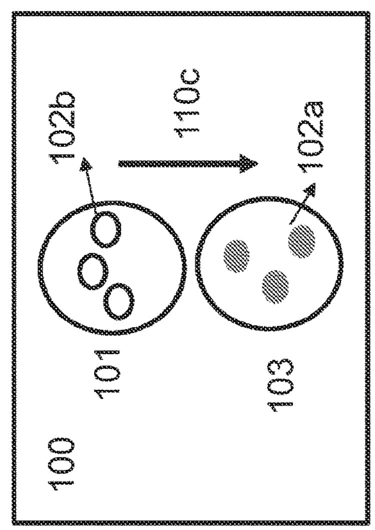
STEP 4
FIG. 1A
110a
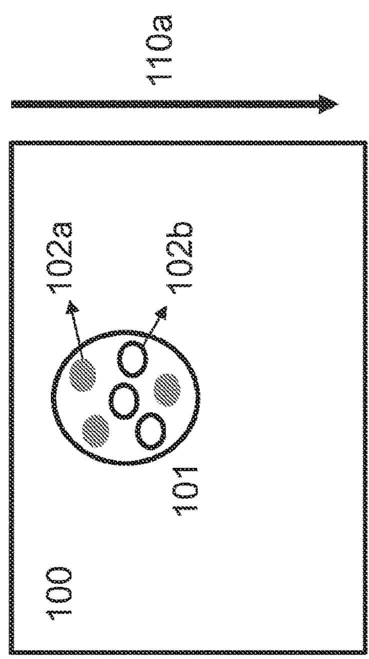
STEP 1
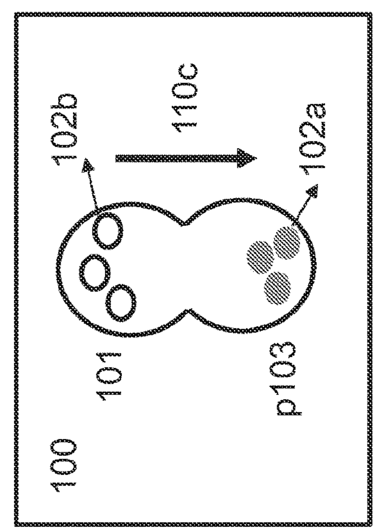
STEP 3

STEP 5

STEP 6

STEP 1

STEP 2

STEP 3

STEP 4

METHODS AND SYSTEMS FOR SEPARATING COMPONENTS OF A BIOLOGICAL SAMPLE WITH GRAVITY SEDIMENTATION

CROSS-REFERENCE TO RELATED APPLICATIONS

This application claims priority to U.S. Provisional Patent Application Ser. No. 62/031,753, filed on Jul. 31, 2014, the disclosure of which is incorporated herein by reference.

INTRODUCTION

Components (e.g., cells) from biological fluids are used in numerous therapeutic, diagnostic and research applications. For example, blood tests often require separation of white blood cells, red blood cells and plasma components. Providing enriched and enhanced preparations of the biological samples, having sufficient concentration for desired therapeutic, diagnostic or research use, can often require numerous and lengthy manipulations. These manipulations can diminish the amount of separated biological material recovered. For example, centrifugation of samples can result in losses because each separated phase of the biological sample cannot be fully recovered. In some cases, multiple iterations of separation, washing and other types of treatments can be deleterious to components of the biological sample causing losses in component viability due to over-processing. Still further, large amounts of the biological fluid may not be readily available. In some cases, only a few microliters of the biological fluid can be made available, making a reduction in processing losses highly impactful.

Isolating and enriching components of a biological sample can vary in degree of selectivity, speed and convenience and can depend not only on the approach and conditions used but also on the geometric configurations of the extraction. There is a constant need for the development of simplified and miniaturized sample preparation methods requiring lower quantities of materials and more efficient ways to obtain isolated and enriched biological samples. Methods and systems that provide improved separation of components of biological samples on small samples with little to no loss are of interest.

SUMMARY

Aspects of the present disclosure include methods for separating components having different densities in a biological sample droplet. Methods according to certain embodiments include contacting a surface of a support with a biological sample droplet that includes components of different densities; subjecting the biological sample droplet to a gravitational force to produce two or more regions in the biological sample droplet on the support surface, where each region in the biological sample droplet includes a component from the biological sample droplet having a different density; separating the biological sample droplet into two or more product droplets, where each product droplet includes a different region of the biological sample droplet; and collecting one or more of the product droplets. Methods, in certain instances also include conveying one or more product droplets along the support surface by applying an electric field to discrete regions of the support. In some embodiment, methods further include washing the product droplets by contacting the product droplet with a wash buffer to produce a washed droplet; subjecting the washed droplet to a gravitational force sufficient to produce two or more regions in the washed droplet on the support surface, where each region in the washed droplet includes a component having a different density; separating the washed droplet into two or more separated washed product droplets, where each separated washed product droplet includes a different region of the washed droplet; and collecting one or more of the separated washed product droplets.

Systems, including a support configured to separate a biological sample droplet into two or more distinct product droplets and an actuator for positioning the support in a manner sufficient to subject the biological sample droplet to a gravitational force suitable for practicing the subject methods are also described.

BRIEF DESCRIPTION OF THE FIGURES

The invention may be best understood from the following detailed description when read in conjunction with the accompanying drawings. Included in the drawings are the following figures:

FIG. 1A depicts a schematic showing the separation of a biological sample droplet into two separated droplets according to certain embodiments.

FIG. 2A shows a side view of a support positioned on a platform positioned at an angle with respect to a plane parallel to the ground. FIG. 2B shows a side view of a support positioned on a platform at a 45° angle with respect to a plane parallel to the ground. FIG. 2C shows a side view of a support position on a platform at a 90° angle with respect to a plane parallel to the ground.

DETAILED DESCRIPTION

Figure 1B:
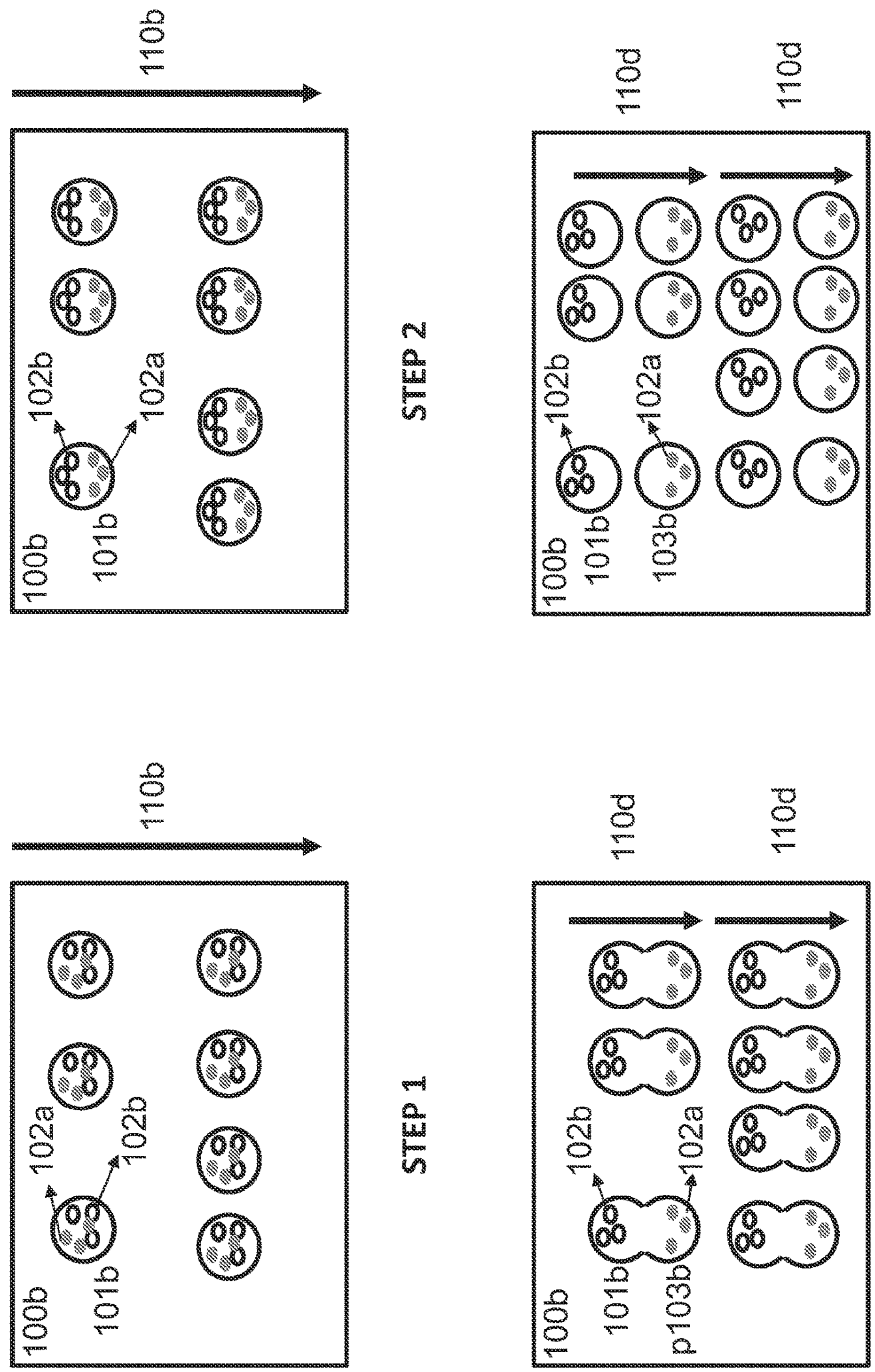
FIG. 1B depicts a schematic showing the separation of an array of biological sample droplets on a support, each biological sample droplet being separated into two distinct droplets according to certain embodiments.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides methods for separating components having different densities from a biological sample droplet. In further describing embodiments of the disclosure, methods for separating components in a biological sample droplet are first described in greater detail. Next, systems suitable for practicing the subject methods are described. Computer systems and kits are also provided.

Methods for Separating Components from a Biological Sample Droplet by Gravity Sedimentation As summarized above, aspects of the present disclosure include methods for separating components of a biological sample droplet by subjecting the biological sample droplet to a gravitational force. The term "separating" is used herein in its conventional sense to refer to the physical separation of a plurality of components based on a particular physical or chemical property such as density of the component. As described in greater detail below, the biological sample droplet is subjected to a gravitational force for a duration sufficient to separate components of the biological sample droplet into two or more regions, each region containing components of different density. In embodiments, components are separated within the biological sample droplet such that each component has a higher concentration in a particular region (e.g., bottom region, upper region, middle region, etc.) as compared to components in a biological sample droplet not subjected to the gravitational force. In other words, components of a biological sample droplet are separated in a manner sufficient to enrich components into particular regions of the biological sample droplet.

For example, the concentration of a component in a particular region of the biological sample droplet (e.g., bottom region, upper region, middle region, etc.) may be increased by 5% or more, such as by 10% or more, such as by 20% or more, such as by 25% or more, such as by 30% or more, such as by 50% or more, such as by 75% or more, such as 90% including by 95% or more. In some instances, the concentration of a component in a particular region of the biological sample droplet may be increased by 2-fold or more, such as by 3-fold or more, such as by 5-fold or more, such as by 7-fold or more and including by 10-fold or more.

In embodiments of the present disclosure, components of the biological sample droplet may be separated into two or more regions such that 5% or more of a certain component is separated in a particular region (e.g., bottom region, upper region, middle region, etc.) of the biological sample droplet, such as 10% or more, such as 20% or more, such as 25% or more, such as 30% or more, such as 40% or more, such as 50% or more, such as 60% or more, such as 70% or more, such as 80% or more, such as 90% or more, such as 95% or more and including separating 99% or more of a component into a particular region of the biological sample droplet. In certain embodiments, 100% of the component is separated into a particular region of the biological sample droplet.

For instance, in one example, the biological sample includes two components and the biological sample droplet is subjected to a gravitational force for a duration sufficient to separate 95% or more of a first component into a first region (e.g., bottom region) of the biological sample droplet and 95% or more of the second component into a second region (e.g., upper region) of the biological sample droplet. In this example, 5% or less of the first component is present in the second region (e.g, upper region) and 5% or less of the second component is present in the first region (e.g., bottom region) after subjecting the biological sample droplet to the gravitational force.

In another example, the biological sample droplet includes two components and the biological sample droplet is subjected to a gravitational force for a duration sufficient to separate 100% or more of a first component into a first region (e.g., bottom region) of the biological sample droplet and 95% or more of the second component into a second region (e.g., upper region) of the biological sample droplet. In this example, none of the first component is present in the second region (e.g., upper region) and 5% or less of the second component is present in the first region (e.g., bottom region) after subjecting the biological sample droplet to the gravitational force.

In yet another example, the biological sample droplet includes three components and is subjected to a gravitational force for a duration sufficient to separate 95% or more of a first component into a first region of the biological sample droplet and 95% or more of a second component and a third component into a second region. In this example, 5% or less of the first component is present in the second region and 5% or less of the second and third components are present in the first region after subjecting the biological sample droplet to the gravitational force.

In yet another example, the biological sample droplet includes three components and is subjected to a gravitational force for a duration sufficient to separate 95% or more of a first component into a first region of the biological sample droplet and 100% or more of a second component and a third component into a second region. In this example, 5% or less of the first component is present in the second region and none of the second and third components are present in the first region after subjecting the biological sample droplet to the gravitational force.

In still another example, the biological sample droplet includes two components and is subjected to a gravitational force for a duration sufficient to separate 100% of the first component into a first region of the biological sample and 100% of the second component into a second region. In this example, none of the first component is present in the second region and none of the second component is present in the first region after subjecting the biological sample droplet to the gravitational force.

In certain embodiments, the biological sample droplet is a whole blood droplet and the whole blood droplet is subjected to a gravitational force for a duration sufficient to separate 5% or more of the red blood cells and white blood cells into a first region of the whole blood droplet (e.g., bottom region), such as 10% or more, such as 25% or more, such as 30% or more, such as 40% or more, such as 50% or more, such as 60% or more, such as 70% or more, such as 80% or more, such as 90% or more, such as 95% or more and including isolating 99% or more of the red blood cells and white blood cells into a first region of the whole blood droplet. In some instances, methods include subjecting the whole blood droplet to a gravitational force for a duration sufficient to separate 100% of the red blood cells and white blood cells into a first region of the whole blood droplet. In these embodiments, the whole blood droplet is subjected to a gravitational force for a duration sufficient to separate 5% or more of the blood plasma into a second region (e.g., upper region) of the whole blood droplet, such as 10% or more, such as 25% or more, such as 30% or more, such as 40% or more, such as 50% or more, such as 60% or more, such as 70% or more, such as 80% or more, such as 90% or more, such as 95% or more and including isolating 99% or more of the blood plasma into a second region (e.g., upper region) of the whole blood droplet.

For example, in some instances the whole blood droplet is subjected to a gravitational force for a duration sufficient to separate 95% or more of the red blood cells and white blood cells into a first region (e.g., bottom region) of the whole blood droplet and 95% or more of the blood plasma into a second region (e.g., upper region). In these instances, 5% or less of the blood plasma is present in the first region (e.g., bottom region) and 5% or less of the red blood cells and white blood cells are present in the second region (e.g., upper region) after subjecting the whole blood droplet to the gravitational force.

In other instances, the whole blood droplet is subjected to a gravitational force for a duration sufficient to separate 100% or more of the red blood cells and white blood cells into a first region (e.g., bottom region) of the whole blood droplet and 95% or more of the blood plasma into a second region (e.g., upper region). In these instances, none of the red blood cells and white blood cells are present in the second region (e.g., upper region) and 5% or less of the blood plasma is present in the first region (e.g., bottom region) after subjecting the whole blood droplet to the gravitational force.

In certain instances, 100% of the red blood cells and white blood cells are separated into a first region (e.g., bottom region) and 100% of the plasma is separated into a second region (e.g., upper region) after subjecting the whole blood droplet to the gravitational force.

As used herein, the term "biological sample" is used in its conventional sense to refer to a subset of plant, fungi, bacteria or animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" may refer to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.)

In certain embodiments, the biological sample contains cells. Suitable cells include eukaryotic cells (e.g., mammalian cells) and/or prokaryotic cells (e.g., bacterial cells or archaeal cells). Samples may be obtained from an in vitro source (e.g., a suspension of cells from laboratory cells grown in culture) or from an in vivo source (e.g., a mammalian subject, a human subject, etc.). In some embodiments, the cellular sample is obtained from an in vitro source. In vitro sources include, but are not limited to, prokaryotic (e.g., bacterial, archaeal) cell cultures, environmental samples that contain prokaryotic and/or eukaryotic (e.g., mammalian, protest, fungal, etc.) cells, eukaryotic cell cultures (e.g., cultures of established cell lines, cultures of known or purchased cell lines, cultures of immortalized cell lines, cultures of primary cells, cultures of laboratory yeast, etc.), tissue cultures, and the like.

In some embodiments, the sample is obtained from an in vivo source and can include samples obtained from tissues (e.g., cell suspension from a tissue biopsy, cell suspension from a tissue sample, etc.) and/or body fluids (e.g., whole blood, fractionated blood, plasma, serum, saliva, lymphatic fluid, interstitial fluid, etc.). In some cases, cells, fluids, or tissues derived from a subject are cultured, stored, or manipulated prior to evaluation. In vivo sources include living multi-cellular organisms and can yield non-diagnostic or diagnostic cellular samples.

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

Methods according to embodiments of the present disclosure separate one or more components of the biological sample droplet into distinct product droplets and may include separating cells from other types of cells, separating cells from non-cellular debris (e.g., cell fragments, fragmented cell membranes, organelles, dead or lysed cells), separating cells from non-cellular macromolecules such as free lipids, proteins, polysaccharides and nucleic acid fragments as well as separating one type of non-cellular macromolecules from other types non-cellular macromolecules. In some embodiments, the subject methods separate cells from non-cellular components of a biological sample. In other embodiments, the subject methods separate two or more different types of cells from each other. In yet other embodiments, the subject methods separate two or more different types of non-cellular components (e.g., polysaccharides and proteins) from each other. In certain embodiments, the biological sample is whole blood and the subject methods separate white blood cells and red blood cells from plasma. In still other embodiments, the biological sample is whole blood and the subject methods separate white blood cells from red blood cells.

As summarized above, components in a biological sample droplet having different densities are separated from each other by subjecting the biological sample droplet to a gravitational force. Upon subjecting the biological sample droplet to a gravitational force, components of higher density separate from components of lower density within the biological sample droplet. After subjecting the biological sample droplet to the gravitational force for a sufficient duration, two or more distinct regions are formed in the biological sample droplet where each region includes components of different densities. For example, a biological sample droplet containing a high density component and a low density component is subjected to a gravitational force sufficient to produce within the biological sample droplet a region with the high density component and a region with the lower density component. As described in greater detail below, a droplet dividing force, such as an electric field applied in an electrowetting protocol, may be applied to the support in a manner sufficient to divide the biological sample droplet into two distinct product droplets on the support. Each product droplet may include one or more components of the biological sample droplet, such as two or more components, such as three or more components and including five or more components, as described below.

FIG. 1A depicts a schematic showing the separation of a biological sample droplet into two separated droplets by subjecting the biological sample droplet to a gravitational force according to embodiments of the present disclosure. At step 1 of FIG. 1A, biological sample droplet 101 contacted with support 100 contains components 102*a* and 102*b* having different densities homogeneously distributed within the biological sample droplet. Subjecting biological sample droplet 101 to a gravitational force 110*a* at step 2 causes component 102*a*, which has a higher density, to settle at the bottom of the droplet (i.e., in the direction of the gravitational force) more than component 102*b*. After subjecting the biological sample droplet to the gravitational force 110*a* for a sufficient duration, the components of the biological sample droplet separate into two regions in the biological sample droplet, each region having components of different density. Here, higher density components 102*a* separate into the lower region of the biological sample droplet and lower density components 102*b* remain in the upper region of the biological sample droplet. (Step 2) Application of a droplet dividing force 110*c*, such as an electric field applied in an eletrowetting protocol causes the biological sample droplet (step 3) to form a pre-separated droplet p103 which begins to divide the biological sample droplet into two product droplets where a first product droplet contains higher density components 102*a* and a second product droplet contains lower density components 102*b*. After application of dividing force 110*c* for a sufficient duration (step 4), product droplet 103 containing higher density component 102*a* and product droplet 101 containing lower density component 102*b* become completely separated from each other. In this embodiment, product droplet 103 retains high density component 102*a*, while product droplet 101 retains lower density component 102*b*.

FIG. 1B depicts a schematic showing the separation of an array of biological sample droplets on a support, each biological sample droplet being separated into two distinct droplets according to embodiments of the present disclosure. At step 1 of FIG. 1B, biological sample droplets 101*b* are contacted with support 100*b*. Each biological sample droplet 101*b* contains components 102*a* and 102*b* having different densities homogeneously distributed within the biological sample droplet. Subjecting the array of biological sample droplets to a gravitational force 110*b* at step 2 causes higher density components 102*a* to begin settling to the bottom of the biological sample droplet. After subjecting the biological sample droplet to the gravitational force for a sufficient duration, the components of each biological sample droplet separate into two regions in the biological sample droplet, each region having components of different density. Here, higher density components 102*a* separate into the lower region of each biological sample droplet and lower density components 102*b* remain in the upper region of each biological sample droplet. Application of a droplet dividing force 110*d*, such as an electric field applied in an eletrowetting protocol, causes each biological sample droplet to form pre-separated droplets p103*b* which begins to divide the region containing higher density components 102*a* from the region containing lower density components 102*b*. After application of dividing force 110*d* for a sufficient duration, fully separated product droplets 103*b* are formed from each of the pre-separated droplets p103*b* (step 3). As discussed above, separated product droplets 103*b* contain higher density components 102*a* while lower density components 102*b* are retained in product droplets 101*b*.

In embodiments, the biological sample droplet is divided into one or more distinct droplets having components of higher density and one or more distinct droplets having components of lower density. By "distinct" and "separated" is meant that the separated product droplets are not in fluid communication with each other. In other words, there is at least some void space between the separated product droplets (i.e., a space or region on the support where no liquid is present). In embodiments, depending on the droplet dividing force employed to divide the biological sample droplet into the product droplets as well as the properties of the biological sample (e.g., fluid viscosity, cellular and non-cellular composition), the distance between each separated droplet may vary, where distinct droplets may be separated by a distance of 0.001 mm or more, such as by 0.005 mm or more, such as by 0.01 mm or more, such as by 0.05 mm or more, such as 0.1 mm or more, such as by 0.5 mm or more, such as by 1 mm or more, such as by 5 mm or more and including by 10 mm or more.

When separated, each distinct product droplet may include one or more components of interest from the biological sample droplet, such as two or more components of interest, such as three or more components of interest, such as 4 or more components of interest and including 5 or more components of interest. For example, where the biological sample droplet includes 4 components having different densities and is separated into two distinct product droplets (i.e., a separated droplet and the remaining portion of the biological sample droplet), a first separated product droplet may include 1 component and a second separated product droplet may include the 3 other components. In other embodiments, a first separated product droplet may include 2 components and a second separated product droplet may include the other 2 components. In still other embodiments, a first separated product droplet may include 3 components and a second separated product droplet may include the remaining 1 component. For example, where the biological sample droplet is whole blood, a first separated product droplet may include red blood cells and a second separated product droplet may include white blood cells and plasma. In other instances, a first separated product droplet may include white blood cells and red blood cells and a second separated product droplet may include plasma.

As described above, the biological sample droplet is subjected to a gravitational force for a duration sufficient to separate components of different density into two or more regions within the biological sample droplet. (e.g., higher density components in a bottom region of the biological sample droplet and lower density components in an upper region of the biological sample droplet) For example, the biological sample droplet may be subjected to a gravitational force for a duration sufficient to separate components of the biological sample by density into three different regions within the biological sample droplet or more, such as four different regions or more and including five different regions or more. In one instance, the biological sample includes two components of interest having different density and methods include subjecting the biological sample droplet to a gravitational force for a duration sufficient to separate the two components of interest by density into two regions within the biological sample droplet. In another instance, the biological sample droplet includes three components of interest having different densities and methods include subjecting the biological sample droplet to a gravitational force for a duration sufficient to separate the three components by density into two different regions within the biological sample droplet. In yet another instance, the biological sample droplet includes three components of interest having different densities and methods include subjecting the biological sample droplet to a gravitational force for a duration sufficient to separate the three components by density into three different regions within the biological sample droplet. In still other instances, the biological sample droplet includes four components of interest having different densities and methods include subjecting the biological sample droplet to a gravitational force for a duration sufficient to separate the four components by density into two different regions within the biological sample droplet (e.g., two higher density components in a bottom region of the biological sample droplet and two lower density components in an upper region of the biological sample droplet; or one higher density component in a bottom region of the biological sample droplet and three lower density components in an upper region of the biological sample droplet)

In some embodiments, the biological sample droplet is a biological sample containing cells and methods of the present disclosure include separating cellular components and non-cellular components of the biological sample droplet into two or more regions within the biological sample droplet. For example, the biological sample droplet is subjected to a gravitational force for a duration sufficient to separate cellular components from non-cellular components into two different regions within the biological sample droplet. (e.g., cellular components in a bottom region of the biological sample droplet and non-cellular components in an upper region of the biological sample droplet)

In other embodiments, the biological sample droplet is a biological sample droplet containing two or more different types of cells and methods include separating each type of cell by density into different regions within the biological sample droplet. For example, in certain instances, the biological sample droplet is a whole blood droplet and methods include separating red blood cells and white blood cells into one region within the biological sample droplet and plasma into a second region within the biological sample droplet (e.g., red blood cells and white blood cells in a bottom region of the whole blood droplet and plasma in an upper region of the whole blood droplet) In other instances, the biological sample droplet includes red blood cells and white blood cells and methods include subjecting the biological sample droplet to a gravitational force sufficient to separate the red blood cells into a first region within the biological sample droplet and the white blood cells into a second region within the biological sample droplet.

After subjecting the biological sample droplet to a gravitational force sufficient to separate components of different densities into two or more regions in the biological sample droplet, the biological sample droplet is divided into two or more product droplets, where each product droplet includes a different region of the biological sample droplet. (e.g., dividing a biological sample droplet having two regions into two product droplets) The biological sample droplet may be divided into two more product droplets by any convenient droplet dividing protocol, as described in greater detail below, such as for example applying an electric field in an electrowetting protocol. Depending on the number of components of interest and regions produced by the applied gravitational force, the biological sample droplet may be divided into two or more product droplets, such as three or more product droplets, such as four or more product droplets and include five or more product droplets.

In some embodiments, the biological sample is a biological sample containing cells and methods of the present disclosure include dividing the biological sample droplet into two or more separated product droplets, where one or more of the product droplets contain cells and one or more of the product droplets contain non-cellular components. In other embodiments, the biological sample contains two or more different types of cells and methods include dividing the biological sample droplet such that each type of cell is divided into distinct product droplets. For example, in certain instances, the biological sample droplet is a whole blood droplet and methods of the present disclosure include dividing the whole blood droplet into a first product droplet containing the cellular components (e.g., red blood cells and white blood cells) and a second product droplet containing plasma. In other embodiments, the whole blood droplet is divided into three product droplets, white blood cells being in a first product droplet, red blood cells in a second product droplet and plasma being in a third product droplet.

In practicing methods of the present disclosure, a biological sample droplet having components of different densities is contacted with a surface of a support and is subjected to a gravitational force for a duration sufficient to separate the components of different density into two or more regions within the biological sample droplet. (e.g., higher density components in a bottom region of the biological sample droplet and lower density components in an upper region of the biological sample droplet). The biological sample droplet is then divided using a droplet dividing protocol into two or more separated product droplets where each product droplet includes one or more regions of the biological sample droplet.

In some embodiments, the biological sample droplet is directly applied to the surface of the support, such as with a pipette, needle with or without a syringe, a manual or mechanical dropper or a computer-automated dropper. In other embodiments, the biological sample droplet is applied to a peripheral position on the support and is conveyed to the desired location on the support by an electrowetting microactuation protocol (as described in greater detail below).

In embodiments, the volume of the biological sample droplet applied to the support surface may vary, for example, ranging in some instances from 0.01 μL to 1000 μL, such as from 0.05 μL to 900 μL, such as from 0.1 μL to 800 μL, such as from 0.5 μL to 700 μL, such as from 1 μL to 600 μL, such as from 2.5 μL to 500 μL, such as from 5 μL to 400 μL, such as from 7.5 μL to 300 μL and including from 10 μL to 200 μL of sample. One or more biological sample droplets may be contacted with the support surface, such as 2 or more biological sample droplets, such as 3 or more, such as 5 or more, such as 10 or more and including contacting 15 or more biological sample droplets with the support surface. Depending on the size of the support surface, the applied biological sample droplets may be spaced apart from each other by 0.1 mm or more, such as by 0.5 mm or more, such as by 1 mm or more, such as by 2 mm or more, such as by 5 mm or more and including by 10 mm or more. The area occupied by each sample droplet will vary, depending on the volume of sample applied and may range from 0.01 to 5 $mm^2$, such as 0.05 to 5 $mm^2$, such as 0.1 to 4.5 $mm^2$, such as 0.25 to 4.5 $mm^2$, such as 0.5 to 4 $mm^2$ and including 1 to 4 $mm^2$.

The size of each applied droplet may be the same or different or some percentage therebetween, as desired. In some embodiments, the size of each applied droplet is the same. In other embodiments, the size of each applied droplet is different and may be selected from a range of droplet sizes. For example, droplets may be applied to the surface in 1 to 10 different sizes, such as 2 to 9 different sizes, such as 3 to 8 different sizes and including 4 to 6 different sizes. Where a range of different droplet sizes are applied to the substrate surface, the percentage of each size of droplet applied to the support surface may vary, where each size constitutes 5% or more of the droplets, such as 10% or more, such as 25% or more, such as 50% or more, such as 75% or more and including 90% or more of the droplets. In still other embodiments, every droplet size applied to the support surface is different. Where the size of the applied droplets are different, the size of the applied droplets on the support may vary by 1% or more, such as by 5% or more, such as by 10% or more, such as by 15% or more, such as by 25% or more, such as by 35% or more, such as by 50% or more, such as by 75% or more, such as by 90% or more and including by 95% or more.

In certain embodiments, each biological sample droplet is contacted with a discrete region on the support surface. As described in greater detail below, each discrete region may include one or more electrodes configured for conveying a fluidic droplet along the surface of the support using an electrowetting microactuation protocol. In some embodiments, each discrete region includes one or more sensors. In these embodiments, the sensors may be configured for determining the presence of a fluidic droplet in the discrete region. In other embodiments, sensors of interest may be configured for determining one or more physical or chemical properties of the droplet positioned in the discrete region. In certain embodiments, a single biological sample droplet is applied in each discrete region.

The biological sample droplets may be applied at any convenient position on the support surface. In some embodiments, the droplets are applied to the support surface in a random pattern. In other embodiments, the droplets are applied in a non-random pattern (i.e., in a predetermined pattern), including in a line pattern or in the pattern of a specific shape (circle, square, triangle, etc.), letter or number configuration. For example, the droplets may be applied to the support surface in a grid pattern.

In practicing the subject methods, the applied biological sample droplet is subjected to a gravitational force. By "gravitational force" is meant an attractive force which acts upon a compound having mass, where resultant movement is in a direction toward the source of the gravitational force. In certain embodiments, the gravitational force is gravity exerted by the Earth and the direction of force exerted on the biological sample droplet is in a direction substantially perpendicular to a plane parallel to the surface of the ground.

In some embodiments, the biological sample droplet is subjected to a gravitational force immediately after the biological sample droplet is contacted with the support. In other embodiments, the biological sample droplet is subjected to the gravitational force a predetermined period of time after contacting with the support. For example, the biological sample droplet may be subjected to a gravitational force 0.01 minutes or more after contacting with the support, such as after 0.05 minutes or more, such as after 0.1 minutes or more, such as after 0.5 minutes or more, such as after 1 minute or more, such as after 5 minutes or more, such as after 10 minutes or more, such as after 15 minutes or more, such as after 30 minutes or more and including subjecting the biological sample droplet to a gravitational force 60 minutes after contacting the biological sample droplet with the support.

In some embodiments, methods include a storage or prefabrication step where the biological sample droplet is a specimen that has been preloaded onto the support surface and is stored on the support for a predetermined period of time before subjecting the biological sample droplet to the gravitational force. The amount of time the biological sample droplet is preloaded and stored on the support surface may vary, such as 0.1 hours or more, such as 0.5 hours or more, such as 1 hour or more, such as 2 hours or more, such as 4 hours or more, such as 8 hours or more, such as 16 hours or more, such as 24 hours or more, such as 48 hours or more, such as 72 hours or more, such as 96 hours or more, such as 120 hours or more, such as 144 hours or more, such as 168 hours or more and including preloading the biological sample droplet onto the support surface 240 hours or more before subjecting the biological sample droplet to a gravitational force. For example, the amount of time the biological sample droplet is preloaded and stored on the support surface may range from 0.1 hours to 240 hours before subjecting the biological sample droplet to a gravitational force, such as from 0.5 hours to 216 hours, such as from 1 hour to 192 hours and including preloading the biological sample droplet onto the support surface from 5 hours to 168 hours before subjecting the biological sample droplet to a gravitational force. For instance, the biological sample may be preloaded onto a support surface at a remote location (e.g., using in a physician's office or outpatient clinic) and sent to a laboratory for processing in accordance with the subject methods. By "remote location" is meant a location other than the location at which the sample is obtained and preloaded onto the support surface. For example, a remote location could be another location (e.g. office, lab, etc.) in the same city, another location in a different city, another location in a different state, another location in a different country, etc., relative to the location of the processing device, e.g., as described in greater detail below. In some instances, two locations are remote from one another if they are separated from each other by a distance of 10 m or more, such as 50 m or more, including 100 m or more, e.g., 500 m or more, 1000 m or more, 10,000 m or more, etc.

In some embodiments, subjecting the biological sample droplet to a gravitational force includes positioning and maintaining the support at an angle with respect to a plane parallel to the surface of the ground. In these embodiments, gravity exerted by the Earth separates components of different density in the biological sample droplet into two or more regions in the biological sample droplet. Depending on the density of the components of the biological sample and the size of biological sample droplet, the angle at which the support is positioned may vary, such as for example, positioning the support at an angle that is 5° or greater with respect to a plane parallel to the surface of the ground, such as at an angle that is 10° or greater, such as at an angle that is 15° or greater, such as at an angle that is 25° or greater, such as at an angle that is 35° or greater, such as at an angle that is 45° or greater, such as at an angle that is 60° or greater, such as at an angle that is 75° or greater, such as at an angle that is 80° or greater and including maintaining the support at an angle that is 90° with respect to a plane parallel to the surface of the ground. In certain embodiments, the support is positioned at an angle that is 45° or greater with respect to a plane parallel to the surface of the ground. In other embodiments, the support is positioned at an angle that is 90° with respect to a plane parallel to the surface of the ground (i.e., directly in line with the direction of the gravitational force). In some instances, the support is positioned at an angle ranging from 5° to 90° with respect to a plane parallel to the surface of the ground, such as at angle from 10° to 85°, such as from 15° to 80°, such as from 20° to 75°, such as from 25° to 70°, such as from 35° to 65° and including 40° to 60 with respect to a plane parallel to the surface of the ground.

Figure 2:
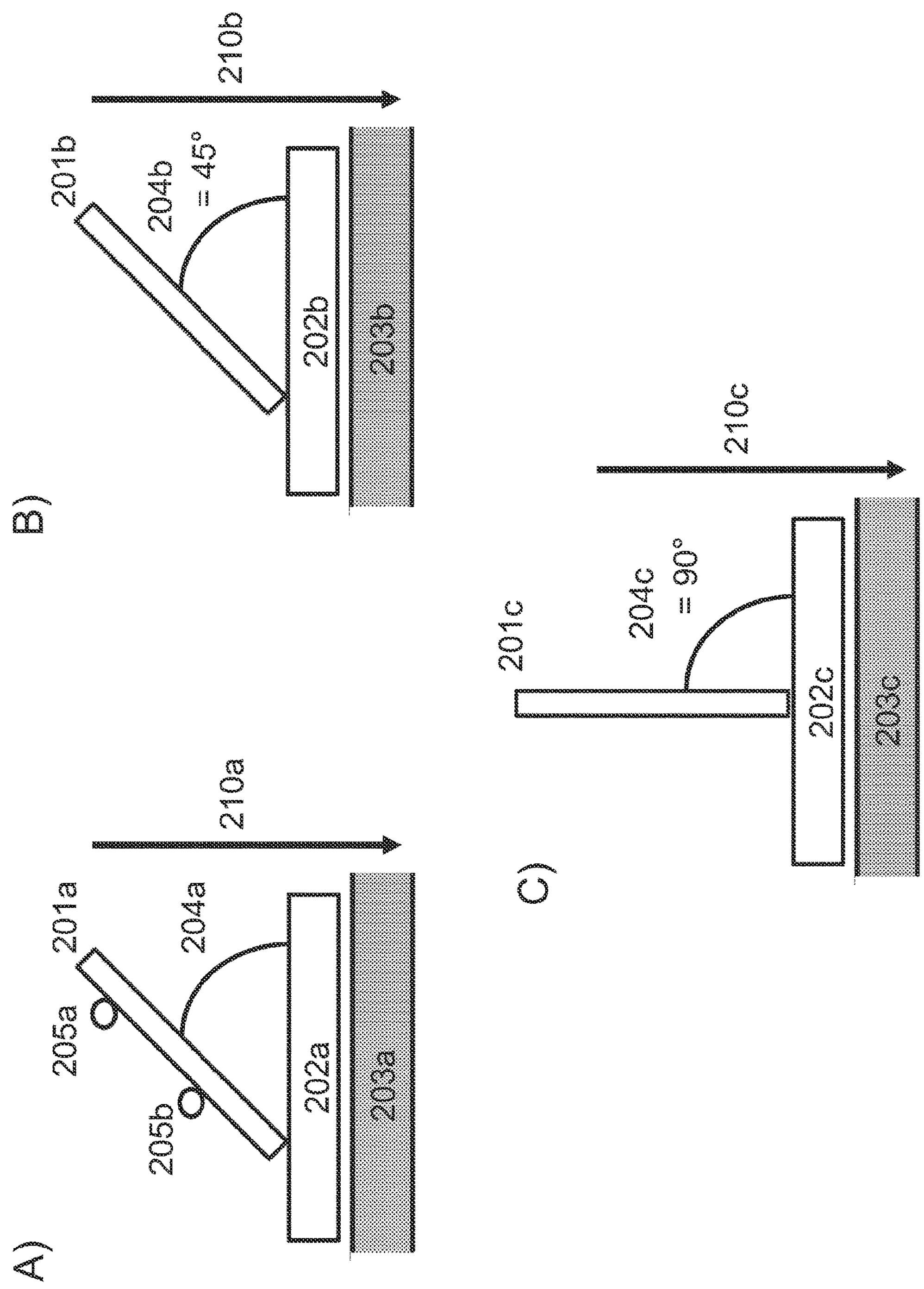
FIGS. 2A-C illustrate configurations for positioning the support according to certain embodiments.

Schematic diagrams in FIGS. 2A-C illustrate configurations for positioning the support according to certain embodiments of the present disclosure. FIG. 2A depicts a side view of a support 201*a* that is positioned on support platform 202*a* at an angle with respect to a plane parallel to the ground 203*a*. Support 201*a* can be positioned at an angle 204*a* which can be varied from 0° to 90° depending on the type of sample and desired separation within the droplets, as discussed above. Biological sample droplets 205*a* and 205*b* positioned on the surface of support 201*a* are subjected to a gravitational force in the direction 210*a* for a duration sufficient to separate the components by density within the droplets. FIG. 2B depicts a side view of support 201*b* positioned on support platform 202*b* at an angle of 45° with respect to a plane parallel to the ground 203*b*. FIG. 2C depicts a side view of support 201*c* positioned on support platform 202*c* at an angle of 90° with respect to a plane parallel to the ground 203*c*.

The biological sample droplet is subjected to a gravitational force for a duration sufficient to separate components of different density into two or more regions within the biological sample droplet. In embodiments, the duration the biological sample droplet is subjected to the gravitational force may vary and may be 0.01 minutes or longer, such as for 0.05 minutes or longer, such as for 0.1 minutes or longer, such as for 0.5 minutes or longer, such as for 1 minute or longer, such as for 3 minutes or longer, such as for 5 minutes or longer, such as for 10 minutes or longer, such as for 15 minutes or longer, such as for 20 minutes or longer, such as for 30 minutes or longer, such as for 45 minutes or longer, such as for 60 minutes or longer and including for 90 minutes or longer. For example, the biological sample droplet may be subjected to the gravitational force for a duration which ranges from 0.01 minutes to 960 minutes, such as from 0.05 minutes to 480 minutes, such as from 0.1 minutes to 240 minutes, such as from 0.5 minutes to 120 minutes, such as from 1 minute to 90 minutes, such as from 5 minutes to 60 minutes and including subjecting the biological sample droplet to the gravitational force for a duration of from 10 minutes to 45 minutes.

The support may be maintained at a single angle or may be changed to a different angle at any time during separation of the biological sample droplets. Where the support is positioned at more than one angle, the duration the support is maintained at each angle may independently be 0.01 minutes or more, such as 0.1 minutes or more, such as 1 minute or more, such as 5 minutes or more, such as 10 minutes or more, such as 30 minutes or more and including 60 minutes or more. The time period between each different angle employed may also vary, as desired, being separated independently by a delay of 1 minute or more, such as 5 minutes or more, such as by 10 minutes or more, such as by 15 minutes or more, such as by 30 minutes or more and including by 60 minutes or more. In embodiments where the support is maintained at more than two (i.e., three or more) angles to subject the biological sample droplet to the gravitational force, the delay between each angle employed may be the same or different.

Depending on the type and number of components of different density in the biological sample the support may be maintained at an angle to subject the biological sample droplet to a gravitational force continuously or in discrete intervals. For example, in some embodiments, the support is maintained at an angle to subject the biological sample droplet to a gravitational force continuously. In other instances, the support is maintained at an angle to subject the biological sample droplet to a gravitational force in discrete intervals, such as for example for intervals of for 0.01 minutes or longer, such as for 0.05 minutes or longer, such as for 0.1 minutes or longer, such as for 0.5 minutes or longer, such as for 1 minute or longer, such as for 3 minutes or longer, such as for 5 minutes or longer, such as for 10 minutes or longer, such as for 15 minutes or longer, such as for 20 minutes or longer, such as for 30 minutes or longer, such as for 45 minutes or longer, such as for 60 minutes or longer and including for 90 minutes or longer. Where the support is maintained at an angle in discrete intervals, methods may include 1 or more intervals, such as 2 or more intervals, such as 3 or more intervals and including 5 or more intervals.

In embodiments of the present disclosure, each step (application of the biological sample droplet to the support, subjecting the biological sample droplet to a gravitational force, dividing the biological sample droplet into two or more separated product droplets and collecting one or more of the separated product droplets) can be carried out at any suitable temperature so long as the viability of the components of the biological sample droplet and separated droplets are preserved as desired. As such, the temperature according to embodiments of the disclosure may vary, such as from −80° C. to 100° C., such as from −75° C. to 75° C., such as from −50° C. to 50° C., such as from −25° C. to 25° C., such as from −10° C. to 10° C., and including from 0° C. to 25° C.

As components of the biological sample droplets are separated by a gravitational force into discrete regions within the biological sample droplet, the amount of time required for separation may depend on the viscosity of the biological fluid sample. For example, the viscosity of biological fluid samples separated in accordance with the subject methods may range in some aspects from about 0.01 cP to about 750 cP, including about 0.1 cP to about 100 cP, such as about 0.1 cP to 50 cP, about 0.2 cP to about 10 cP, about 0.2 cP to about 2.0 cP, about 0.5 to 1.5 cP, or about 0.75 cP to 1.5 cP. In some instances, the viscosity of the biological fluid sample has a viscosity substantially equal to that of water at the given temperature (e.g., about 1 cP at 20° C., about 0.65 cP at 40° C.).

In some embodiments, methods further include agitating the support. Agitation may include, but is not limited to applying ultrasound to the biological sample droplet on the support, shaking the support either manually (i.e., by hand) or mechanically (i.e., by a mechanically or electrically powered shaking device), among other agitating protocols. Depending on the properties of the biological sample droplet (e.g., viscosity, cellular components) as well as the angle at which the support is maintained, the support may be agitated for any amount of time, such as for one second or longer, such as for two seconds or longer, such as for 5 seconds or longer, such as for 10 seconds or longer, such as for 30 seconds or longer, such as for 1 minute or longer, such as for 5 minutes or longer, such as for 10 minutes or longer and including agitating the support for 30 minutes or longer. In certain embodiments, the support is agitated while being positioned at an angle to subject the biological sample droplet to a gravitational force.

Where necessary, the parameters for subjecting droplets of interest to a gravitational force may be changed at any time during methods of the present disclosure. For example, the positioning angle of the support, the duration the droplet is subjected to the gravitational force, heating or cooling of the sample and agitation frequency and duration may be changed one or more times during the subject methods, such as two or more times, such as three or more times and including five or more times.

In some embodiments, the positioning angle of the support with respect to a plane parallel to the ground may be changed. For example, the positioning angle of the support may be increased or decreased by 1° or more, such as by 3° or more, such as by 5° or more, such as by 8° or more, such as by 10° or more and increasing or decreasing the positioning angle of the support by 15° or more.

In other embodiments, the duration the biological sample droplet is subjected to the gravitational force may be changed. For example, the duration the biological sample droplet is subjected to the gravitational force may be increased or decrease by 0.01 minutes or longer, such as by 0.05 minutes or longer, such as by 0.1 minutes or longer, such as by 0.5 minutes or longer, such as by 1 minute or longer, such as by 3 minutes or longer, such as by 5 minutes or longer, such as by 10 minutes or longer, such as by 15 minutes or longer, such as by 20 minutes or longer, such as by 30 minutes or longer, such as by 45 minutes or longer, such as by 60 minutes or longer and including by 90 minutes or longer.

In yet other embodiments, the temperature while subjecting the biological sample to the gravitational force may be changed. For example, the temperature may be raised or lower by 0.1° C. or more, such as by 0.5° C. or more, such as by 1° C. or more, such as by 2° C. or more, such as by 5° C. or more and including raising or lowering the temperature by 8° C. or more.

In certain embodiments, methods include monitoring the biological sample droplet while separating components of different density into the two or more regions within the biological sample droplet. Monitoring separation may include assessing (either by a human or with the assistance of a computer, if using a computer-automated process initially set up under human direction) the extent of component separation within the biological sample droplet. For example, monitoring separation of components by density into the two or more regions within the biological sample droplet may include determining by optical absorbance the boundary between a region within the biological sample droplet containing plasma and a region containing cells. Monitoring separation of components into regions within the biological sample droplet may include assessing the physical and chemical properties of the components in each region within the biological sample droplet. Any convenient protocol can be employed to monitor the biological sample droplet, including but not limited to optical absorption, laser scatter, fluorescence, phosphorescence, chemiluminescence, diffuse reflectance, electrochemical sensing, infrared spectroscopy, among other sensing protocols.

In some instances, monitoring includes collecting real-time data, such as employing a detector (e.g., laser scatter detector, optical absorption detector, electrochemical sensor). In other instances, monitoring includes assessing the biological sample droplet at regular intervals, such as every 0.01 minutes, every 0.05 minutes, every 0.1 minutes, every 0.5 minutes, every 1 minute, every 5 minutes, every 10 minutes, every 30 minutes, every 60 minutes or some other interval.

Methods of the present disclosure may also include a step of assessing the biological sample droplet to identify any desired adjustments to the subject protocol. In other words, methods in these embodiments include providing feedback based on monitoring the biological sample droplet, where adjustments to the protocol may vary in terms of goal, where in some instances the desired adjustment are adjustments that ultimately result in an improved separation of components by density within the biological sample droplet, such as providing faster separation, improved purity or increased component enrichment of the components into the two or more regions within the biological sample droplets.

Where feedback provided indicates that a particular protocol is less than optimal, such as where component separation into regions within the biological sample droplet requires too much time or where component separation provides separated regions within the biological sample droplet with insufficient enrichment (e.g., components of different density are undesirably mixed together in a region of the biological sample droplet), methods may include changing one or more parts of the subject protocols. For example, one or more parameters for subjecting the biological sample droplet to a gravitational force may be adjusted. In one example, methods include adjusting the positioning angle of the support (as described above). In another example, methods include changing (increasing or decreasing) the duration the biological sample droplet is subjected to the gravitational force. In yet another example, methods include heating or cooling the biological sample droplet. In still another example, methods include implementing or increasing the magnitude of agitation to the biological sample droplet while subjecting the droplet to the gravitational force.

For instance, where the duration required to separate components of different density into separated regions within the biological sample droplet is less than optimal (e.g., longer than desired), methods may include increasing the magnitude of the gravitational force, such as by increasing the angle the support is positioned with respect to the ground. In another instance, where component separation within the biological sample droplet provides separated regions having insufficient enrichment (i.e., components of different density are not separated from each other to the extent desired), methods may include increasing the duration the biological sample droplet is subjected to the gravitational force or increasing the magnitude of the gravitational force, such as by increasing the angle the support is positioned with respect to the ground.

In some embodiments, where a single interval is not sufficient to provide the desired extent of component separation within the biological sample droplet, methods may include conducting one or more additional intervals. In these embodiments, protocols described herein for subjecting a biological sample droplet to a gravitational force to separate components of different density into two or more regions within the biological sample droplet are repeated one or more times in a sequential manner. In practicing the subject methods, multiple interval protocols may include two or more intervals, such as three or more intervals, such as four or more intervals, such as five or more intervals, including ten or more intervals.

Aspects of the present disclosure also include dividing the biological sample into two or more product droplets. In practicing the subject methods, a droplet dividing force (e.g., mechanical agitation or electric field) is applied for a duration sufficient to separate the biological sample droplet into two or more separated product droplets. Each separated product droplet includes one or more of the regions having components of different density produced within the biological sample droplet as described above.

By "separated product droplets" is meant that product droplets prepared by the subject methods are not in fluid communication with each other. In other words, there is at least some void space between each product droplet. In embodiments, depending on the protocol employed to divide the biological sample droplet into product droplets, the distance formed between each product droplet may vary, where product droplets may be separated by a distance of 0.001 mm or more, such as by 0.005 mm or more, such as by 0.01 mm or more, such as by 0.05 mm or more, such as 0.1 mm or more, such as by 0.5 mm or more, such as by 1 mm or more, such as by 5 mm or more and including by 10 mm or more.

When separated, each product droplet may include one or more components of interest from the biological sample droplet, such as two or more components of interest, such as three or more components of interest, such as 4 or more components of interest and including 5 or more components of interest. For example, where the biological sample droplet includes 4 components having different densities and is separated into two product droplets, a first product droplet may include 1 component of interest and the a second product droplet may include 3 components of interest. In other embodiments, a first product droplet may include 2 components of interest and a second product droplet may include 2 components of interest. In some instances, the biological sample droplet is whole blood and a first product droplet includes red blood cells and a second droplet includes white blood cells and plasma. In other instances, a first product droplet includes white blood cells and red blood cells and a second product droplet includes plasma.

In certain embodiments, the biological sample droplet is divided into more than two separated droplets. For example, the biological sample droplet may be separated into 3 or more droplets, such as 4 or more droplets and including 5 or more droplets. In one instance, the biological sample droplet includes 2 components of interest having different densities and the biological sample droplet is divided into 2 product droplets, where each product droplet containing a component of different density. In other instances, the biological sample droplet includes 3 components each having different densities and the biological sample droplet is divided into 3 product droplets, where each product droplet containing a component of different density. In yet other instances, the biological sample droplet includes 4 components each having different densities and the biological sample droplet is divided into 4 product droplets, where each product droplet containing a component of different density. In still other instances, the biological sample droplet includes 4 components of interest and the biological sample droplet is divided into 3 product droplets, where a first product droplet includes two components, a second product droplet includes 1 component and a third product droplet includes 1 component.

In some embodiments, the biological sample droplet is a biological sample containing cells and methods include dividing the biological sample droplet into two or more product droplets, where one or more of the product droplets contain cells and one or more of the product droplets contain non-cellular components. In other embodiments, the biological sample droplet contains two or more different types of cells and methods include dividing the biological sample droplet into two or more product droplets, where each product droplet includes a distinct type of cell. For example, in certain instances, the biological sample droplet is whole blood and methods include dividing the biological sample droplet into a first product droplet containing red blood cells and white blood cells and a second product droplet containing plasma. In other embodiments, the biological sample droplet includes red blood cells and white blood cells and method include dividing the biological sample droplet into a first product droplet containing red blood cells and a second product droplet containing white blood cells.

Any convenient protocol may be employed to divide the biological sample droplet into two or more product droplets, including but not limited to mechanical agitation, applying ultrasound, microfluidic protocols, applying a magnetic field and applying an electric field, among other separation protocols. In certain embodiments, the biological sample droplet is divided into two or more product droplets by an electrowetting protocol. The term "electrowetting" is used herein in its conventional sense to refer to protocols for applying an electric field to the surface of the support through an array of electrodes to actuate, mix, agitate, dispense, split or transport fluidic droplets on the surface of a support. For example, in some embodiments the support is configured with an array of electrodes to apply an electric field to the support and divide the biological sample droplet into two or more product droplets.

By employing an electrowetting microactuation protocol, dividing the biological sample droplet into product droplets can be controlled as desired. In certain embodiments, the biological sample droplet is positioned on top of one electrode while partially overlapping a second electrode on one side and third electrode on the opposite side. Activation of each electrode causes the biological sample droplet to spread across each of the three electrodes. Deactivation of the first electrode results in splitting of the biological sample droplet into two product droplets a first product droplet positioned on top of the second electrode and a second product droplet positioned on top of the third electrode.

In some embodiments, electrowetting protocols for dividing the biological sample droplet into two or more product droplets may include, but are not limited to those described in U.S. Pat. Nos. 6,565,727; 6,773,566; 6,911,132; 7,547,380; 7,329,545; 8,349,276; 8,470,153 and 8,613,889, the disclosures of which are herein incorporated by reference.

In practicing the subject methods, one or more of the product droplets may be collected. In some embodiments, all of the separated product droplets are collected. Collecting product droplets may include combining the droplets together at a predetermined location on the support or the product droplets may be removed from the support altogether, as desired. In some embodiments, collecting product droplets include combining the droplets together at a predetermined location on the support, such as for example at a peripheral edge or at a corner of the support. In other embodiments, collecting product droplets include removing the droplets from the support and retaining the droplets in a collection reservoir.

Where more than one biological sample droplet (e.g., a plurality of whole blood droplets) is applied to the support, separated product droplets having the same biological sample components may be collected and combined together at a predetermined location on the support. For example, each of the plurality of biological sample droplets may be divided into a first product droplet containing a first component, a second product droplet containing a second component and a third product droplet containing a third component. In this example, each of the first product droplets may be combined together, each of the second product droplets may be combined together or each of the third product droplets may be combined together.

Product droplets containing components of the biological sample may be collected at any time after dividing the biological sample droplet. In some embodiments, the product droplets are collected 1 minute or greater after the separated droplets are prepared, such as 2 minutes or greater, such as 3 minutes or greater, such as 5 minutes or greater, such as 10 minutes or greater and including 30 minutes or greater after dividing the biological sample droplet.

In certain embodiments, product droplets are collected by conveying the droplets across the support to a collection location along a predetermined path. In some instances, the conveyance path for collecting the product droplets is along the perimeter of the support. In other instances, product droplets are collected and the conveyance path is in line with each of the product droplets.

Any convenient protocol may be employed to convey and collect the product droplets along the support. In certain embodiments, product droplets are conveyed and collected along the support surface by an electrowetting protocol. As discussed above, "electrowetting" refers to protocols for applying an electric field to the surface of the support through an array of electrodes to move, mix, agitate, dispense, split or transport fluidic droplets on the surface of a support. For example, in some embodiments the support is configured with an array of electrodes to move the separated droplets along predetermined paths across the support surface.

By employing an electrowetting microactuation protocol, movement by droplets on the support can be controlled as desired. In certain embodiments, the subject droplet is positioned on top of one electrode while partially overlapping a second electrode. Activation of the first and second electrode causes the droplet to spread a portion of the droplet across the second electrode. Deactivation of the first electrode results in movement of the droplet from the first electrode to the second electrode. In this embodiment, the second electrode is located adjacent to the first electrode along a first direction. To convey the droplet across the support additional electrodes positioned in the first direction are sequentially activated and deactivated, resulting in movement of the droplet along a predetermined path in the first direction. Additional directions for conveying the droplets as well as additional paths along the support surface may be employed by controlling activation and deactivation of an array or network of electrodes, as desired.

Depending on the size of the support and droplets being moved, the number of electrode activation and deactivation cycles along a predetermined path may vary, such as 5 or more cycles, such as 10 or more, such as 15 or more, such as 25 or more and including 50 or more electrode activation and deactivation cycles.

In some embodiments, the electrode array is configured to combine droplets, such as at a collection location on the support. Droplets may be combined together by moving the plurality of droplets (either sequentially or simultaneously) to the same location on the support. In these embodiments, droplets may also be mixed. For example, in some instances droplets may be conveyed to the same location and passively mixed together by diffusion. In other instances, the combined droplets are actively mixed, such as by agitating the combined droplets by varying the frequency of the applied electric field at the collection location. In certain embodiments, droplets are mixed by rotating the combined droplets in a circular motion on the support by activating and deactivating electrodes at the collection location in a circular pattern. Actuation by rotating the combined droplets in a circular pattern mixes the droplets by creating a turbulent non-reversible flow on the surface of the support as well as forming dispersed multilaminates which enhance mixing of the droplets.

In some embodiments, electrowetting protocols for moving droplets along the surface of support of interest may include, but are not limited to those described in U.S. Pat. Nos. 6,565,727; 6,773,566; 6,911,132; 7,547,380; 7,329,545; 8,349,276; 8,470,153 and 8,613,889, the disclosures of which are herein incorporated by reference.

In certain embodiments, methods further include assessing the collected droplets. For example, assessing the collected droplets may include determining the physical and chemical properties of the collected droplets. The physical and chemical properties of the collected droplets may be assessed with any convenient protocol, such as for example, by UV-vis spectrometry, IR spectroscopy, nuclear magnetic resonance spectroscopy, mass spectrometry, flame ionization spectrometry, high-performance liquid chromatography, among other analysis protocols.

In some instances, assessing the physical or chemical properties of the collected droplets includes collecting real-time data, such as employing a detector (e.g., laser scatter detector, optical absorption detector, electrochemical sensor) at the collection location on the support. In other instances, monitoring includes assessing the physical or chemical properties of the collected droplets at regular intervals, such as every 0.01 minutes, every 0.05 minutes, every 0.1 minutes, every 0.5 minutes, every 1 minute, every 5 minutes, every 10 minutes, every 30 minutes, every 60 minutes or some other interval.

As discussed above, one or more of the product droplets may be collected and removed from the support. In certain instances, one or more product droplets may be left on the support (i.e., are not collected or removed from the support) and may be subjected to one or more additional separation intervals. In these embodiments, the subsequent separation intervals may include contacting product droplets of interest with wash buffer to produce a washed product droplet.

In some embodiments, the wash buffer is directly applied to the droplets remaining on the surface of the support. In other embodiments, the wash buffer is applied to a peripheral position on the support and conveyed across the support and combined with the subject droplets by an electrowetting protocol.

Each of the subject droplets may be combined with the same or different volume of wash buffer. The volume of wash buffer combined with each droplet may vary, such as for example, ranging from 0.01 μL to 1000 μL, such as from 0.05 μL to 900 μL, such as from 0.1 μL to 800 μL, such as from 0.5 μL to 700 μL, such as from 1 μL to 600 μL, such as from 2.5 μL to 500 μL, such as from 5 μL to 400 μL, such as from 7.5 μL to 300 μL and including from 10 μL to 200 μL of wash buffer.

The wash buffer may be any suitable aqueous or organic liquid buffer composition so long as the buffer is not deleterious or degrade the desired components of the droplet. For example, wash buffers of interest may include, but are not limited to, PBS (phosphate) buffer, acetate buffer, N,N-bis(2-hydroxyethyl)glycine (Bicine) buffer, 3-{[tris(hydroxymethyl)methyl]amino}propanesulfonic acid (TAPS) buffer, 2-(N-morpholino)ethanesulfonic acid (MES) buffer, citrate buffer, tris(hydroxymethyl)methylamine (Tris) buffer, N-tris(hydroxymethyl)methylglycine (Tricine) buffer, 3[N-Tris(hydroxymethypmethylamino]-2-hydroxypropanesulfonic Acid (TAPSO) buffer, 4-2-hydroxyethyl-1-piperazineethanesulfonic acid (HEPES) buffer, 2-{[tris(hydroxymethyl)methyl]amino}ethanesulfonic acid (TES) buffer, piperazine-N,N'-bis(2-ethanesulfonic acid) (PIPES) buffer, dimethylarsinic acid (Cacodylate) buffer, saline sodium citrate (SSC) buffer, 2(R)-2-(methylamino)succinic acid (succinic acid) buffer, potassium phosphate buffer, N-Cyclohexyl-2-aminoethanesulfonic acid (CHES) buffer, among other types of wash buffer solutions.

In some embodiments, the washed droplets are then subjected to a gravitational force and divided into two or more product droplets with an electrowetting protocol, such as described above. The washed droplets may be subjected to a gravitational force immediately after the subject droplets are combined with the wash buffer. In other embodiments, the washed droplets are subjected to a gravitational force a predetermined period of time after the subject droplets are combined with the wash buffer, such as for example, 0.01 minutes or more after the wash buffer is combined with the subject droplets, such as after 0.05 minutes or more, such as after 0.1 minutes or more, such as after 0.5 minutes or more, such as after 1 minute or more, such as after 5 minutes or more, such as after 10 minutes or more, such as after 15 minutes or more, such as after 30 minutes or more and 60 or more.

Figure 3:
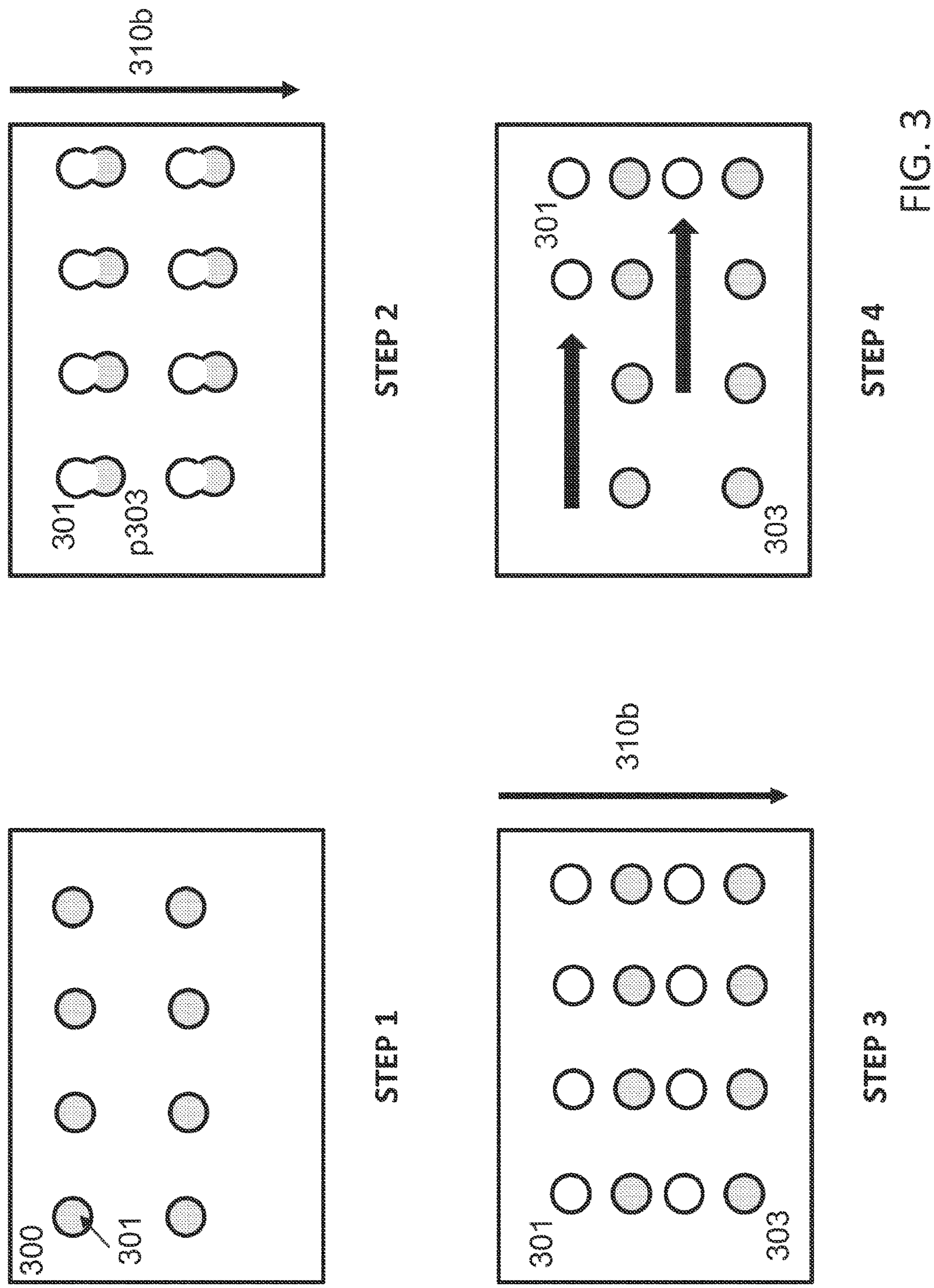
FIG. 3 depicts a step-wise schematic showing a separation protocol of an array of biological sample droplets on a support according to certain embodiments.
Figure 3:
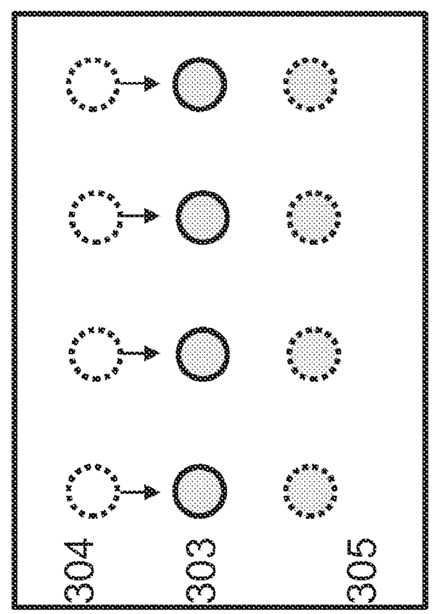
Figure 3:
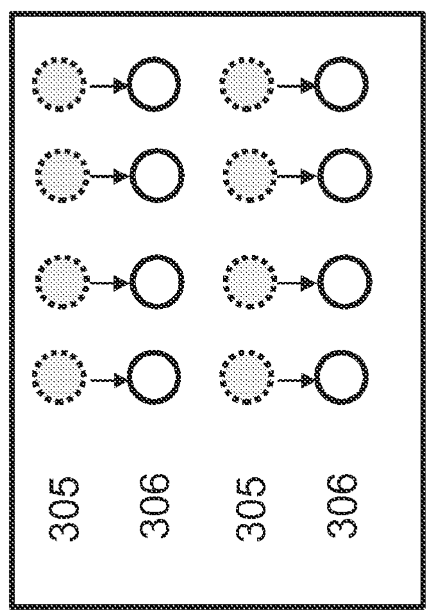

FIG. 3 depicts a schematic showing the separation of an array of biological sample droplets on a support, where a first product droplet is removed from the support and a second product which is retained on the support, is washed with a wash buffer droplet. At step 1, biological sample droplets 301 are contacted with support 300. Subjecting the array of biological sample droplets to a gravitational force causes components which have a higher density to settle to the bottom region of the biological sample droplets while components having a lower density remain in the upper region of the biological sample droplets. Application of a droplet dividing force 310*b*, such as an electric field applied in an electrowetting protocol causes each biological sample droplet 301 to begin separating forming pre-separated product droplets p303 which begins to divide the biological sample droplet into two or more product droplets. After subjecting the array of biological sample droplets to dividing force 310*b* (e.g., electric field) for a sufficient duration, fully separated product droplets 303 are formed from each of the pre-separated droplets p303 (step 3). Using an electrowetting protocol, the remaining portion of biological sample droplets 301 are removed from the support (step 4). Wash buffer droplets 304 are contacted with the support and using an electrowetting protocol, wash buffer droplets 304 are combined with product droplets 303 to form an array of washed product droplets 305 (step 5). In certain embodiments, the above steps are repeated (step 6) on the washed product droplets 305 (i.e., subjecting the droplets to a gravitational force followed by dividing the droplets with a droplet dividing protocol) to form a second set of product droplets 306 from washed product droplets 305, where product droplet 305 and product droplet 306 contain components of a biological sample droplet having different densities.

Figure 4:
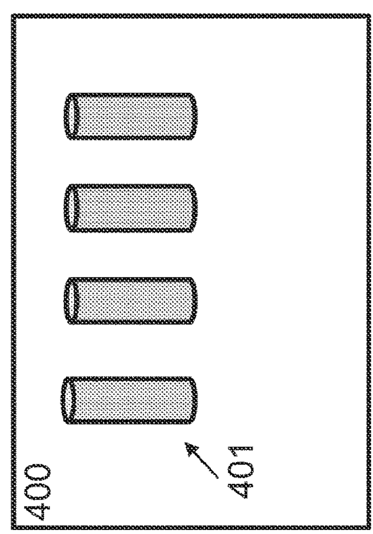
FIG. 4 depicts a step-wise schematic showing a separation protocol of an array of biological sample droplets on a support according to certain other embodiments.
Figure 4:
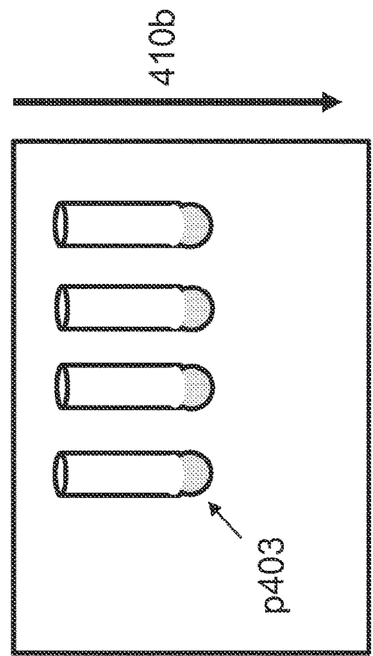
Figure 4:
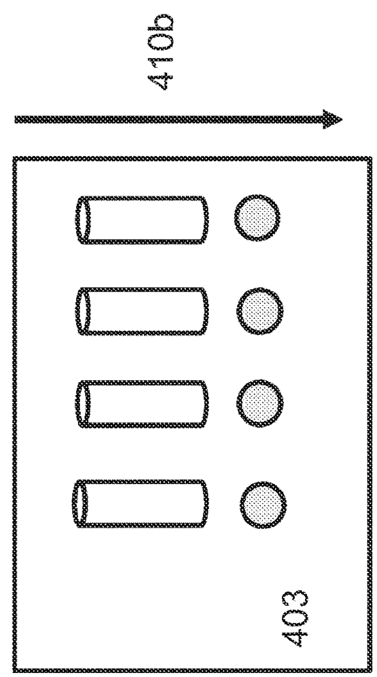
Figure 4:
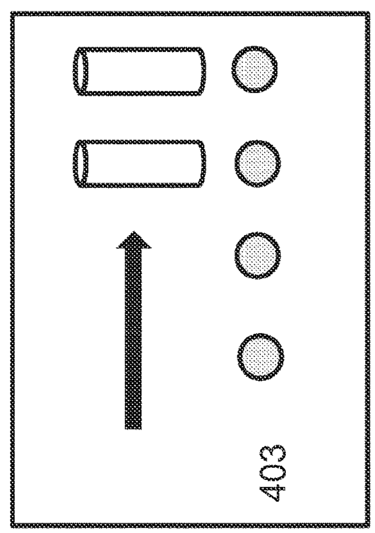
Figure 4:
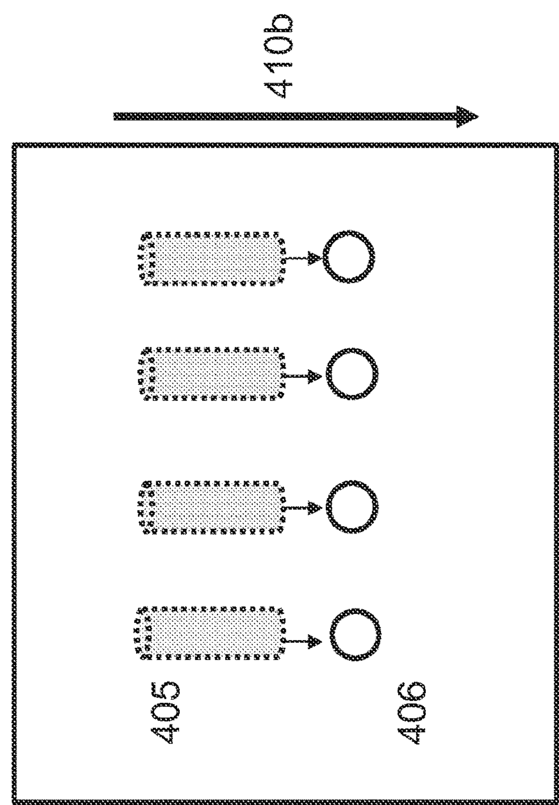
Figure 4:
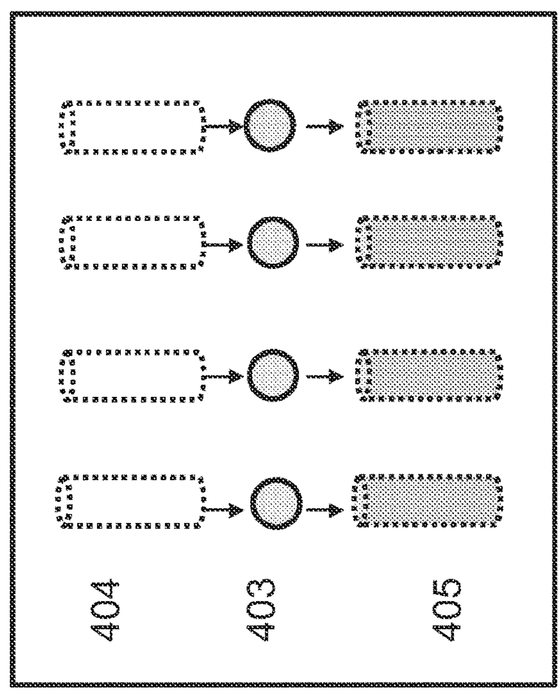

FIG. 4 depicts a schematic showing the separation of an array of biological sample columns on a support, where the remaining portion of each biological sample column is removed from the support and each of the separated droplets, which remain on the support, are washed with a column of wash buffer applied to the support. At step 1, biological sample columns 401 are contacted with support 400. Subjecting the array of biological sample columns to a gravitational force causes components which have a higher density to settle to the bottom region of the biological sample columns while components having a lower density remain in the upper region of the biological sample columns. At step 2, a dividing force 410*b*, such as an electric field applied in an electrowetting protocol, causes each biological sample column 401 to begin forming pre-separated product droplets p403 containing higher density components. After subjecting the array of biological sample columns to dividing force (e.g., electric field) 410*b* for a sufficient duration, fully separated product droplets 403 are formed from each of the pre-separated droplets p403 (step 3). Using an electrowetting protocol, the remaining portion of biological sample columns 401 are removed from the support (step 4). Columns of new wash buffer 404 are contacted with the support. Using an electrowetting protocol, wash buffer columns 404 are combined with product droplets 403 to form an array of washed sample columns 405 (step 5). In certain embodiments, the above steps are repeated (step 6) on the washed sample columns 405 (i.e., subjecting the columns to a gravitational force followed by separating out droplets from the columns with a droplet dividing protocol) to form a second set of product droplets 406 from washed sample columns 405, where product droplet 406 contain components of a biological sample droplet having a different density than components in product droplet 403.

Systems for Separating Components from a Biological Sample Droplet by Gravity Sedimentation Aspects of the present disclosure include systems for separating components of a biological sample droplet by subjecting the biological sample droplet to a gravitational force. As discussed above, by "separating components", the subject systems isolate one or more components of the biological sample droplet into distinct product droplets and in some embodiments may be configured to separate cells from other types of cells, separate cells from non-cellular debris (e.g., cell fragments, fragmented cell membranes, organelles, dead or lysed cells), separate cells from non-cellular macromolecules such as free lipids, proteins, polysaccharides and nucleic acid fragments as well as separate one type of non-cellular macromolecule from other types non-cellular macromolecules. In certain embodiments, the subject systems are configured to separate components of whole blood, such as separating white blood cells and red blood cells from plasma or separating white blood cells from red blood cells.

As summarized above, systems include a support configured to separate a biological sample droplet into two or more product droplets and an actuator for positioning the support in a manner sufficient to subject the biological sample droplets to a gravitational force.

In embodiments, the support is a solid support which can suitably accommodate one or more applied biological sample droplets. The support may be made of any suitable material so long as it does not degrade or have any deleterious effects on the components of the biological sample and biological sample droplets can be separated into two or more product droplets. Suitable materials for supports may include, but are not limited to glass, plastic or polymeric materials such as thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate). In some embodiments, the support is a dielectric material, such as a vapor deposited dielectric, including parylene C (e.g., deposited on glass), parylene N; Teflon AF; Cytop, a film dielectric including polyimide film (Kapton), fluorinated polymers such as fluorinated ethylene propylene (FEP) including perfluoroethylenepropylene copolymer, polytetrafluoroethylene (PTFE), perfluoralkoxy polymers and copolymers, cyclic olefin polymers and copolymers as well as polyethylenes or may be a non-dielectric material configured with a hydrophobic coating, such as Teflon AF, Cytop, Fluoropel coatings, silane coatings, fluorosilane coatings among other types of materials. The dielectric constant of support materials of interest may vary, ranging from 2 to 100, such as from 3 to 90, such as from 4 to 80, such as from 5 to 70, such as from 6 to 60, such as from 8 to 50 and including from 10 to 40.

The size of the support may vary, ranging in some instances from 0.25 $cm^2$ to 1000 $cm^2$, such as 0.5 $cm^2$ to 750 $cm^2$, such as 0.75 $cm^2$ to 500 $cm^2$, such as 1 $cm^2$ to 250 $cm^2$, and including 2.5 $cm^2$ to 100 $cm^2$. The thickness of the support may also vary, ranging in some instances from 0.1 mm to 10 mm, such as from 0.5 mm to 8 mm, such as from 0.75 mm to 6 mm and including ranging from 1 mm to 5 mm. The support may be any desired shape, such a circle, oval, half-circle, crescent-shaped, star-shaped, square, triangle, rhomboid, pentagon, hexagon, heptagon, octagon, rectangle or other suitable polygon.

Where desired, the support may be flexible or rigid. The term "flexible" is used in its conventional sense to mean that the support is a planar support that is capable of being bent without breaking or otherwise able to be turned, bowed, or twisted, without breaking. In these embodiments, the support may be pliable and is not rigid or stiff. In other embodiments, the support is rigid. The term "rigid" is used in its conventional sense to mean that the support is a planar support which is stiff and not capable of substantially being bent without breaking.

In some embodiments, systems of interest include a support coupled with one or more electrodes configured to apply an electric field (such as in an electrowetting protocol) to divide the biological sample droplet into two or more product droplets, as described above. In addition, the support may include one or more electrodes configured to apply an electric field to move droplets on the surface of the support. In certain embodiments, systems may include an array or network of electrodes coupled to the support. For example, systems of interest may include supports coupled to an array of electrode having 2 electrodes or more, such as 5 electrodes or more, such as 10 electrodes or more, such as 15 electrodes or more, such as 25 electrodes or more and including an array having 50 electrodes or more.

The array of electrodes may further include electrical connections for electrically coupling electrodes to external circuitry. The array of electrodes may also include electrical connections for electrically coupling certain electrodes together. In one example, the support includes two or more electrodes associated with the support, and includes a source of electricity for activating and deactivating each electrode. For instance, each electrode may be electronically coupled to and controlled by a set of manual switches or a computer-controlled processor coupled to electronic circuitry for activating and deactivating each electrode.

In some embodiments, systems are configured to supply a voltage to the electrodes. Depending on the thickness and dielectric constant of the support, systems may be configured to apply a voltage to the electrodes in a range from 0.001 V to 1000 V, such as from 0.005 V to 750 V, such as from 0.01 V to 500 V, such as from 0.05 V to 250 V, such as from 0.1 V to 200 V and including from 1 V to 100 V.

In certain embodiments, systems of interest include electrode arrays and accompanying electronic circuitry for manipulating droplets (moving, dividing, etc.) on the surface of a support such as those described in U.S. Pat. Nos. 6,565,727; 6,773,566; 6,911,132; 7,547,380; 7,329,545; 8,349,276; 8,470,153 and 8,613,889, the disclosures of which are herein incorporated by reference.

In certain embodiments, the support is configured as an array of discrete regions. The discrete regions may have a random or non-random pattern, including patterns of specific shapes (circle, square, triangle or other polygon), letter or number configurations or image configurations. In certain instances, the support has a grid pattern of discrete regions. For example, the grid pattern may be composed of equally sized squares or rectangles.

Each discrete location on the support may be the same or different size, as desired and may range from 0.01 to 5 $cm^2$, such as 0.05 to 5 $cm^2$, such as 0.1 to 4.5 $cm^2$, such as 0.25 to 4.5 $cm^2$, such as 0.5 to 4 $cm^2$ and including 1 to 4 $cm^2$. Each discrete region may also have the same or different physical properties from each other, such as size, electrical conductivity, surface wettability, etc. Where the subject systems include an array or network of electrodes (as described above), each discrete region may include one or more electrodes, such as two or more electrodes and including three or more electrodes in each discrete region.

In some embodiments, each discrete region includes one or more sensors. In these embodiments, the sensors may be configured for determining the presence of a fluidic droplet in the discrete region. In other embodiments, sensors of interest may be configured for determining one or more physical or chemical properties of the droplet positioned in the discrete region. Sensor protocols of interest may include, but not limited to laser scatter detectors, optical absorption detectors, electrochemical sensors, voltage sensors, among other types of sensors.

As summarized above, systems also include an actuator for positioning the support in a manner sufficient to subject droplets on the support to a gravitational force. As discussed above, subjecting the biological sample droplet to a gravitational force, according to certain embodiments, includes positioning and maintaining the support at an angle with respect to a plane parallel to the surface of the ground such that gravity exerted by the Earth separates components of different density into two or more regions within the biological sample droplet. In embodiments, the actuator is configured to position the support at an angle with respect to a plane parallel to the ground. The actuator may be configured to position and maintain the support at any desired angle, such as at an angle that is 5° or greater with respect to a plane parallel to the surface of the ground, such as at an angle that is 10° or greater, such as at an angle that is 15° or greater, such as at an angle that is 25° or greater, such as at an angle that is 35° or greater, such as at an angle that is 45° or greater, such as at an angle that is 60° or greater, such as at an angle that is 75° or greater, such as at an angle that is 80° or greater and including maintaining the support at an angle that is 90° with respect to a plane parallel to the surface of the ground. In certain embodiments, the actuator is configured to position and maintain the support at an angle that is 45° or greater with respect to a plane parallel to the surface of the ground. In other embodiments, the actuator is configured to position and maintain the support at an angle that is 90° with respect to a plane parallel to the surface of the ground (i.e., directly in line with the direction of the gravitational force) In other instances, the actuator is configured to position and maintain the support ranging from 5° to 90° with respect to a plane parallel to the surface of the ground, such as at angle from 10° to 85°, such as from 15° to 80°, such as from 20° to 75°, such as from 25° to 70°, such as from 35° to 65° and including 40° to 60° with respect to a plane parallel to the surface of the ground.

Any actuation protocol may be employed to position the support at the desired angle. In some embodiments, the support may be coupled to a platform with a hinge or latch at a proximal edge of the support where the actuator positions the support at an angle by raising the distal edge of the support. In other embodiments, the actuator may be a lift column that is coupled to the bottom of the support and positioning of the support by the actuator at an angle includes adjusting a pivot or rocker.

In some instances, actuation of the support to the desired angle is carried out manually (i.e., positioning of the support by hand). In other instances, the actuator is a mechanical actuation device, such as for example a mechanical leadscrew assembly or a mechanically operated geared translation device. In yet other embodiments, the actuator is a motor-driven displacement device, such as a motor actuated displacement stage, motor driven leadscrew assembly, motor-operated geared actuation device employing a stepper motor, servo motor, brushless electric motor, brushed DC motor, micro-step drive motor, high resolution stepper motor, among other types of motors.

In certain embodiments, the actuator is computer controlled, where systems of interest may also include a processor operably coupled to the actuator, the processor having memory with instructions stored thereon, the instruction including algorithm for actuating the support and positioning the support at a desired angle with respect to a plane parallel to the ground. Where the actuator is operably coupled to a processor for computer controlled actuation of the support, the subject systems may include both hardware and software components for controlling the actuator. For example, the hardware components may take the form of one or more computers, servers, such that the functional elements, i.e., those elements of the system that carry out specific tasks (such as managing input and output of information, processing information, etc.) of the system may be carried out by the execution of software applications on and across the one or more computer platforms represented of the system.

In these embodiments, systems may include a display and operator input devices, such as for example a keyboard, mouse, or the like for inputting desired parameters for actuating the support to the desired position. For example, parameters of interest may include the desired angle for positioning the support, the duration the support is maintained at the angle as well as any scheduled changes to the positioning of the support.

The processor may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The processor memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

Memory may be any suitable device in which the processor can store and retrieve data, such as magnetic, optical, or solid state storage devices (including magnetic or optical disks or tape or RAM, flash drive, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e., smartphone).

In some embodiments, systems according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In some embodiments, systems may further include a biological sample storage reservoir configured to dispense one or more biological sample droplets to the support. The biological sample storage reservoir may be any suitable reservoir that is capable of storing and dispensing biological sample to the support. The biological sample storage reservoir may be in fluid communication with the support and may be configured to provide 1 or more different types biological sample droplets, such 2 or more different types of biological sample droplets, such as 3 or more different types of biological sample droplets, such as 5 or more different types of biological sample droplets and including 10 or more different types of biological sample droplets. Depending on the particular design of the biological sample storage reservoir, systems may further include one or more inlets for delivering the biological sample to the support. In certain embodiments, systems of interest include one or more reservoirs in fluid communication with an electrowetting microactuator configured to dispense a biological sample droplet to a peripheral edge of the support and move the biological sample droplet to the desired location on the support.

Systems of the present disclosure may also include a wash buffer storage chamber configured to deliver one or more wash buffer droplets or columns of wash buffer to the support. The wash buffer storage chamber may be any suitable solvent reservoir that is capable of storing and providing one or more wash buffers to the support to combine with the one or more droplets prepared on the support. The wash buffer chamber may be in fluid communication with one or more sources of wash buffer and may be a single high throughput storage reservoir which can provide wash buffer as desired for contacting with droplets on the support. As discussed above, systems may include a wash buffer that is an aqueous or organic liquid buffer composition which is not deleterious or will not degrade the desired components of the biological sample droplet. For example, wash buffers of interest may include, but are not limited to, PBS (phosphate) buffer, acetate buffer, N,N-bis (2-hydroxyethyl)glycine (Bicine) buffer, 3-{[tris(hydroxymethyl)methyl]amino}propanesulfonic acid (TAPS) buffer, 2-(N-morpholino)ethanesulfonic acid (MES) buffer, citrate buffer, tris(hydroxymethyl)methylamine (Tris) buffer, N-tris (hydroxymethyl)methylglycine (Tricine) buffer, 3[N-Tris (hydroxymethypmethylamino]-2-hydroxypropanesulfonic Acid (TAPSO) buffer, 4-2-hydroxyethyl-1-piperazineethanesulfonic acid (HEPES) buffer, 2-{[tris(hydroxymethyl)methyl]amino}ethanesulfonic acid (TES) buffer, piperazine-N,N'-bis(2-ethanesulfonic acid) (PIPES) buffer, dimethylarsinic acid (Cacodylate) buffer, saline sodium citrate (SSC) buffer, 2(R)-2-(methylamino)succinic acid (succinic acid) buffer, potassium phosphate buffer, N-Cyclohexyl-2-aminoethanesulfonic acid (CHES) buffer, among other types of wash buffer solutions.

The source of one or more wash buffers may be a reservoir with pre-measured aliquots for contacting with a predetermined number of droplets. For example, source of one or more wash buffers may include reservoirs which have pre-measured aliquots for contacting with 2 droplets or more, such as 3 droplets or more, such as 5 droplets or more, such as 10 droplets or more, such 25 droplets or more, such as 50 droplets or more and including pre-measured aliquots for contacting with 100 droplets or more. The one or more sources may include a single type of wash buffer or may be capable of providing a plurality of different types of wash buffers as desired. For example, the source may be capable of storing and providing, as desired, 2 different types of wash buffers or more, such as 3 different types of wash buffers or more, such as 5 different types of wash buffers or more, and including 10 different types of wash buffers or more. Depending on the particular design of the wash buffer chamber, the chamber may further include one or more inlets for delivering the wash buffer to the support to contact with the support. In certain embodiments, systems of interest include one or more reservoirs in fluid communication with an electrowetting microactuator configured to dispense wash buffer at a peripheral edge of the support and move the wash buffer droplets to the desired location on the support.

Computer Controlled Systems

Aspects of the present disclosure may further include computer controlled systems for practicing the subject methods, where the systems further include one or more computers for automation or semi-automation of a system for practicing methods described herein. In embodiments, systems include a computer having a computer readable storage medium with a computer program stored thereon, where the computer program when loaded on the computer includes algorithm for subjecting a biological sample droplet positioned on a support to a gravitational force; algorithm for dividing the biological sample droplet into two or more product droplets and algorithm for collecting one or more of the separated droplets. In certain embodiments, the computer program may also include algorithm for providing a biological sample droplet from a biological sample source to the surface of a support. For example, where the biological sample droplet is applied to the support by an electrowetting microactuation protocol, the computer processor may also include algorithm for moving the contacted biological sample droplet to a desired location on the support.

In embodiments, the computer controlled system includes an input module and a processing module. In some embodiments, the subject systems may include an input module such that parameters or information about each biological sample (type of sample, viscosity of fluid, droplet size, number of droplets), components from the biological sample that are of interest, the positioning angle for subjecting the biological sample to a gravitational force, the temperature of the support, agitation frequency, information about the wash buffer and number of separation intervals, etc. may be inputted into the computer. The processing module includes memory having a plurality of instructions for performing certain steps of the subject methods, such as actuating a support to position and maintain the support at an angle sufficient to subject the biological sample droplet to a gravitational force as well as instructions for dispensing and collecting the separated droplets. In addition, the processing module may include memory having a plurality of instructions for applying a droplet dividing force, such as an electric field in an electrowetting protocol, in a manner sufficient to divide the biological sample droplet into two or more product droplets.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Computer systems of interest may include a display and operator input device. Operator input devices may, for example, be a keyboard, mouse, or the like. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e., smartphone).

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Windows 8, iOS, Sun Solaris, Linux, OS/400, Compaq Tru64 Unix, SGI IRIX, Siemens Reliant Unix, and others.

Utility

The subject supports, systems, methods and computer systems find use in a variety of applications where it is desirable to separate components of a sample in a fluid medium. In some embodiments, the present disclosure finds use in preparing purified components of a biological sample such a whole blood sample where it is desirable to obtain isolated components of blood (e.g., white blood cells, red blood cells, platelets, plasma, etc.) Embodiments of the present disclosure also find use in miniaturized sample preparation where only small quantities of sample are available or where minimizing sample loss during enrichment of a biological sample component is important.

The present disclosure finds use in applications where components (e.g., cells or non-cellular macromolecules such as proteins and polysaccharides) prepared from a biological sample may be desired for research, laboratory testing or for use in therapy. In some embodiments, the subject methods and systems may facilitate obtaining individual cells prepared from a target fluidic or tissue biological sample. For example, the subject methods and systems facilitate obtaining cells from fluidic or tissue samples to be used as a research or diagnostic specimen for diseases such as cancer. Likewise, the subject methods and systems facilitate obtaining cells from fluidic or tissue samples to be used in therapy. Methods and devices of the present disclosure allow for separating and collecting cells from a biological sample (e.g., organ, tissue, tissue fragment, fluid) with enhanced efficiency and low cost.

Kits

Aspects of the invention further include kits, where kits include one or more supports as described herein. In some instances, the kits can include one or more separation protocol components (e.g., buffers) such as described above. In some instances, the kits may further include a sample collection device, e.g., a lance or needle configured to prick skin to obtain a whole blood sample, a pipette, etc., as desired.

The various assay components of the kits may be present in separate containers, or some or all of them may be pre-combined. For example, in some instances, one or more components of the kit, e.g., the supports, are present in a sealed pouch, e.g., a sterile foil pouch or envelope.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Notwithstanding the appended clauses, the disclosure set forth herein is also defined by the following clauses:

1. A method comprising:

contacting a surface of a support with a biological sample droplet, wherein the biological sample droplet comprises components of different densities;

subjecting the biological sample droplet to a gravitational force to produce two or more regions in the biological sample droplet, wherein each region in the biological sample droplet comprises a component from the biological sample having a different density;

separating the biological sample droplet into two or more product droplets, wherein each product droplet comprises a different region of the biological sample droplet; and collecting one or more of the separated product droplets.

2. The method according to clause 1, wherein subjecting the biological sample droplet to a gravitational force comprises maintaining the support in a vertical position sufficient to produce the two or more regions in the biological sample droplet on the support surface by gravity sedimentation.

3. The method according to clause 2, wherein subjecting the biological sample droplet to a gravitational force comprises maintaining the support at an angle that is 45 degrees or greater with respect to a plane parallel to the ground.

4. The method according to clause 2, wherein subjecting the biological sample droplet to a gravitational force comprises maintaining the support at an angle that is 90 degrees with respect to a plane parallel to the ground.

5. The method according to any one of clauses 1-4, wherein the biological sample droplet occupies a discrete position on the support.

6. The method according to clause 5, wherein the discrete position comprises an electrode configured to apply an electric field to the support at the discrete position.

7. The method according to clause 6, wherein the electric field is sufficient to divide the biological sample droplet into two or more separated product droplets comprising components of different densities.

8. The method according to clause 7, wherein the method further comprises applying an electric field to the support in a manner sufficient to move one or more of the separated product droplets along the surface of the support.

9. The method according to clause 8, wherein the product droplet is moved along a predetermined path on the surface of the support.

10. The method according to clause 9, wherein a plurality of product droplets are combined at a predetermined region of the support.

11. The method according to any one of clauses 1-10, further comprising contacting one or more of the separated product droplets with a wash buffer droplet to produce a washed droplet.

12. The method according to clause 11, wherein the wash buffer droplet is contacted with a peripheral edge of the support and moved across the support.
13. The method according to clause 11, wherein the wash buffer droplet is directly contacted with one or more of the separated product droplets.
14. The method according to clause 11, wherein the wash buffer droplet is mixed with one or more of the separated product droplets.
15. The method according to clause 11, further comprising:
subjecting the washed droplet to a gravitational force sufficient to produce two or more regions in the washed droplets, wherein each region in the washed droplet comprises a component having a different density;
separating the washed droplet into two or more separated washed product droplets, wherein each separated washed product droplet comprises a different region of the washed droplet; and
collecting one or more of the separated washed product droplets.
16. The method according to any one of clauses 1-15, wherein the biological sample droplet is subjected to a gravitational force for 5 minutes or longer.
17. The method according to any one of clauses 1-15, wherein the biological sample droplet is subjected to a gravitational force for 30 minutes or longer.
18. The method according to any one of clauses 1-15, wherein the method comprises contacting the biological sample droplet at a peripheral edge of the support and moving the biological sample droplet to a discrete position on the support.
19. A method comprising:
contacting a surface of a support with a biological sample droplet comprising a non-cellular component and a cellular component;
subjecting the biological sample droplet to a gravitational force to produce two or more regions in the biological sample droplet, wherein each region in the biological sample droplet comprises a component from the biological sample having a different density;
dividing the biological sample droplet into two or more product droplets wherein each product droplet comprises a different region of the biological sample droplet; and
collecting one or more of the separated product droplets.
20. The method according to clause 19, wherein the biological sample droplet occupies a discrete position on the support.
21. The method according to clause 20 wherein the discrete position comprises an electrode configured to apply an electric field to the support at the discrete position.
22. The method according to clause 21, wherein the electric field is sufficient to divide the biological sample droplet into two or more separated product droplets, wherein each product droplet comprises a cellular component or non-cellular component of the biological sample droplet.
23. The method according to clause 22, wherein a first product droplet comprises a cellular component and a second product droplet comprises a non-cellular component.
24. The method according to clause 22, wherein a first product droplet comprises two or more cellular components and a second product droplet comprises a non-cellular component.
25. The method according to clause 22, further comprising collecting the first product droplet.
26. The method according to clause 22, further the second product droplet.
27. The method according to any one of clauses 19-26, wherein the method further comprises applying an electric field to the support in a manner sufficient to move one or more of the separated product droplets along the surface of the support.
28. The method according to clause 27, wherein the product droplet is moved along a predetermined path along the surface of the support.
29. The method according to clause 22, wherein the method comprises collecting non-cellular component droplets.
30. The method according to clause 29, wherein collecting non-cellular component droplets comprises combining non-cellular component droplets together at predetermined location on the support
31. The method according to clause 22, wherein the method comprises collecting cellular component droplets.
32. The method according to clause 31, wherein collecting cellular component droplets comprises combining cellular component droplets together at predetermined location on the support.
33. The method according to any one of clauses 19-32 wherein the biological sample droplet is a whole blood droplet.
34. The method according to clause 33, wherein the method comprises separating the biological sample droplet into a first product droplet comprising red blood cells and white blood cells and a second product droplet comprising plasma.
35. The method according to clause 33, wherein the method comprises separating the biological sample droplet into a first product droplet comprising plasma, a second product droplet comprising red blood cells and a third product droplet comprising white blood cells.
36. The method according to any one of clauses 19-35 wherein the biological sample droplet is subjected to a gravitational force for 5 minutes or longer.
37. The method according to any one of clauses 19-35 wherein the biological sample droplet is subjected to a gravitational force for 30 minutes or longer.
38. The method according to any one of clauses 19-37, wherein subjecting the biological sample droplet to a gravitational force comprises maintaining the support at an angle that is 45 degrees or greater with respect to a plane parallel to the ground.
39. The method according to any one of clauses 19-38, wherein subjecting the biological sample droplet to a gravitational force comprises maintaining the support at an angle that is 90 degrees with respect to a plane parallel to the ground.
40. A system comprising:
a support configured to separate a biological sample droplet into two or more distinct product droplets having different densities; and
an actuator for positioning the support at an angle with respect to a plane parallel to the ground sufficient to subject the biological sample to a gravitational force.
41. The system according to clause 40, wherein the actuator is configured to position the support at an angle that is 45 degrees or greater with respect to a plane parallel to the ground.
42. The system according to clause 41, wherein the actuator is configured to position the support at an angle that is 90 degrees with respect to a plane parallel to the ground.
43. The system according to any one of clauses 40-42 further comprising a processor operably coupled to the actuator, wherein the processor comprises a memory with instructions thereon, the instructions comprising an algorithm for positioning the support at an angle from 0 degrees to 90 degrees with respect to a plane parallel to the ground.

44. The system according to any one of clauses 40-43, wherein the actuator is coupled to the support at a peripheral edge of the support.

45. The system according to any one of clauses 40-44, wherein the actuator is coupled to the support on a bottom surface of the support.

46. The system according to any one of clauses 40-45, wherein the surface of the support is divided into discrete regions.

47. The system according to clause 46, wherein the support has a grid pattern of discrete regions.

48. The system according to clause 47, wherein the grid pattern comprises 25 or more discrete regions.

49. The system according to clause 47, wherein the support further comprises an array of electrodes beneath the support.

50. The system according to clause 49, wherein each discrete region comprises an electrode.

51. The system according to clause 49, wherein each discrete region comprises two or more electrodes.

52. The system according to clause 49, wherein the array of electrodes is configured to apply an electric field to the support in a manner sufficient to divide a biological sample droplet into two or more separated product droplets on the support.

53. The system according to clause 52, wherein the array of electrodes is configured to apply an electric field to the support in a manner sufficient to move one or more of the product droplets along the surface of the support.

54. The system according to clause 53, wherein the array of electrodes is configured to apply an electric field to the support in a manner sufficient to move one or more of the product droplets to a peripheral edge of the surface of the support.

55. The system according to clause 46, wherein each discrete region comprises a sensor.

56. The system according to clause 55, wherein the sensor is an electrochemical sensor.

57. The system according to clause 55, wherein the sensor is an optical sensor.

58. The system according to clause 55, wherein the sensor is configured to determine the presence of a fluidic sample in the discrete region.

59. The system according to clause 58, wherein the system further comprises a processor comprising a memory operably coupled to the processor, wherein the memory includes instructions for determining the presence of a fluidic sample at each discrete region.

60. The system according to clause 55, wherein the sensor is configured to determine one or more properties of the fluidic sample in the discrete region.

61. The system according to clause 60, wherein the system further comprises a processor comprising a memory operably coupled to the processor, wherein the memory includes instructions for determining one or more properties of the fluidic sample at each discrete region.

62. The system according to any one of clauses 40-61, wherein the system further comprises a source of biological sample droplet.

63. The system according to any one of clauses 40-62, wherein the system further comprises a source of a wash buffer.

64. A system for separating a biological fluid droplet into two or more droplets comprising components having different densities, the system comprising:

a processor comprising a memory operably coupled to the processor, wherein the memory includes instructions stored thereon, the instructions comprising:

instructions for contacting a biological sample droplet to a surface of a support, wherein the biological sample comprises components of different densities;

an algorithm for positioning the support at an angle from 0 degrees to 90 degrees with respect to a plane parallel to the ground to subject the biological sample droplet to a gravitational force sufficient to produce two or more regions in the biological sample droplet, wherein each region in the biological sample droplet comprises a component from the biological sample having a different density;

an algorithm for applying a droplet dividing force to the biological sample droplet in a manner sufficient to divide the biological sample droplet into two or more product droplets, wherein each product droplet comprises a different region of the biological sample droplet; and an algorithm for collecting one or more of the separated droplets.

65. The system according to clause 64, wherein the memory further comprises instructions for contacting wash buffer with one or more of the separated product droplets.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method comprising:

contacting a surface of a support with a biological sample droplet, wherein the biological sample droplet comprises components of different densities;

subjecting the biological sample droplet to a gravitational force to produce two or more regions in the biological sample droplet, wherein each region in the biological sample droplet comprises a component from the biological sample having a different density;

separating the biological sample droplet into two or more product droplets, wherein each of the two or more product droplets comprises a different region of the biological sample droplet; and collecting one or more of the product droplets.

2. The method according to claim 1, wherein subjecting the biological sample droplet to a gravitational force comprises maintaining the support in a vertical position sufficient to produce the two or more regions in the biological sample droplet on the support surface by gravity sedimentation.

3. The method according to claim 1, wherein the method further comprises applying an electric field to the support in a manner sufficient to:

divide the biological sample droplet into the two or more separated product droplets, wherein each of the two or more product droplets comprises a cellular component or non-cellular component; and move one or more of the separated two or more product droplets along the surface of the support.

4. The method according to claim 3, wherein a first product droplet comprises two or more cellular components and a second product droplet comprises a non-cellular component.

5. The method according to claim 3, wherein the biological sample droplet comprises whole blood and the method comprises separating the whole blood droplet into a first product droplet comprising plasma, a second product droplet comprising red blood cells and a third product droplet comprising white blood cells.

6. The method according to claim 4, further comprising collecting one or more of the of the first and second product droplets.

7. The method according to claim 4, wherein the method further comprises collecting the first product droplet.

8. The method according to claim 7, wherein the collected first product droplet comprises a red blood cell.

9. The method according to claim 7, wherein the collected first product droplet comprises a white blood cell.

10. The method according to claim 3, further comprising:

contacting one or more of the two or more separated product droplets with a wash buffer droplet to produce a washed droplet;

subjecting the washed droplet to a gravitational force sufficient to produce two or more regions in the washed droplet, wherein each region in the washed droplet comprises a component having a different density;

separating the washed droplet into two or more separated washed product droplets, wherein each of the two or more separated washed product droplets comprises a different region of the washed droplet; and collecting one or more of the two or more separated washed product droplets.

11. A method comprising:

contacting a surface of a support with a biological sample droplet comprising a non-cellular component and a cellular component;

subjecting the biological sample droplet to a gravitational force to produce two or more regions in the biological sample droplet, wherein each region in the biological sample droplet comprises a component from the biological sample having a different density;

dividing the biological sample droplet into two or more product droplets wherein each of the two or more product droplets comprises a different region of the biological sample droplet; and collecting one or more of the separated two or more product droplets.

12. The method according to claim 11, wherein the biological sample droplet occupies a discrete position on the support.

13. The method according to claim 12, wherein the discrete position comprises an electrode configured to apply an electric field to the support at the discrete position.

14. The method according to claim 13, wherein the electric field is sufficient to divide the biological sample droplet into two or more separated product droplets, wherein each of the separated two or more product droplets comprises a cellular component or non-cellular component of the biological sample droplet.

15. The method according to claim 14, further comprising collecting a product droplet.

16. A system comprising:

a support configured to separate a biological sample droplet into two or more distinct product droplets having different densities; and an actuator for positioning the support at an angle with respect to a plane parallel to the ground sufficient to subject the biological sample to a gravitational force to separate a biological sample droplet into two or more distinct product droplets having different densities.

17. The system according to claim 16, further comprising an array of electrodes beneath the support and configured to apply an electric field to the support in a manner sufficient to divide a biological sample droplet into two or more separated product droplets on the support and to move one or more of the two or more separated product droplets along the surface of the support.

18. The system according to claim 16, wherein the surface of the support is divided into discrete regions.

19. The system according to claim 18, wherein each discrete region of the discrete regions comprises a sensor configured to determine one or more of:

the presence of a fluidic sample in the discrete region; and one or more properties of the fluidic sample in the discrete region.

20. The system according to claim 18, wherein the system further comprises one or more of a source of biological sample droplet and a source of a wash buffer.

* * * * *